US010113152B1

(12) United States Patent
Abrahamson et al.

(10) Patent No.: US 10,113,152 B1
(45) **Date of Patent: *Oct. 30, 2018**

(54) VARIANT POLYPEPTIDES CAPABLE OF AMINATING ALIPHATIC ALPHA KETO ACIDS

(71) Applicant: AbbVie Inc., North Chicago, IL (US)

(72) Inventors: Michael J. Abrahamson, Chicago, IL (US); Rajarathnam E. Reddy, Gurnee, IL (US); William T. Riordan, Libertyville, IL (US); Sanjay R. Chemburkar, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/873,706

(22) Filed: Oct. 2, 2015

Related U.S. Application Data

(60) Provisional application No. 62/059,538, filed on Oct. 3, 2014.

(51) Int. Cl.

| | |
|---|---|
| ***C12N 9/04*** | (2006.01) |
| ***C12N 9/06*** | (2006.01) |
| *C07H 21/04* | (2006.01) |
| *C12N 15/00* | (2006.01) |

(52) U.S. Cl.
CPC .... *C12N 9/0016* (2013.01); *C12Y 104/01009* (2013.01)

(58) Field of Classification Search
None
See application file for complete search history.

(56) References Cited

U.S. PATENT DOCUMENTS

| | | | |
|---|---|---|---|
| 4,952,496 | A | 8/1990 | Studier et al. |
| 5,693,489 | A | 12/1997 | Studier et al. |
| 5,869,320 | A | 2/1999 | Studier et al. |
| 9,809,534 | B1 | 11/2017 | Lukin et al. |
| 9,809,576 | B1 | 11/2017 | Cink et al. |
| 2011/0229940 | A1 | 9/2011 | Nojiri et al. |

FOREIGN PATENT DOCUMENTS

| | | | |
|---|---|---|---|
| WO | WO-2008/067981 | A2 | 6/2008 |
| WO | WO-2010/030359 | A2 | 3/2010 |
| WO | WO-2010/050516 | A1 | 5/2010 |

OTHER PUBLICATIONS

Branden et al. introduction to Protein Structure, Garland Publishing Inc., New York, p. 247, 1991.*
Nierman Q9A6L1—UniProtKB database, 2013.*
Kaneko. Q8YZN1—UniProtKB database. May 3, 2013.*
(Continued)

*Primary Examiner* — Yong D Pak
(74) *Attorney, Agent, or Firm* — Dana M. Gordon; Foley Hoag LLP

(57) ABSTRACT

Disclosed are, among other things, variant polypeptides, nucleic acids encoding the polypeptides, production of the variant polypeptides, and use of the variant polypeptides in various applications, such as screening and synthetic methods. For example, the variant polypeptides, or enzymatically-active fragments thereof, are useful for converting aliphatic keto acids to aliphatic alpha amino acids.

14 Claims, 5 Drawing Sheets

Specification includes a Sequence Listing.

(56) References Cited

OTHER PUBLICATIONS

Studer. Residue mutations and their impact on protein structure and function: detecting beneficial and pathogenic changes. Biochemical Journal Jan. 9, 2013, 449 (3) 581-594.*

Faucher, A.M. et al., "Synthesis of BILN 2061, an HCV NS3 Protease Inhibitor with Proven Antiviral Effect in Humans," Org Lett, 6(17):2901-04 (2004).

Wang, X.J. et al., "Efficient Synthesis of (S)-2-(Cyclopentyloxycarbonyl)-amino-8-nonenoic Acid: Key Building Block for BILN 2061, an HCV NS3 Protease Inhibitor," Org Process Res Dev, 11:60-3 (2007).

Park et al., "Asymmetric Syntheses of iso-Boc (S)-2-Amino-8-nonenoic Acid in One Through-Process," Org Process Res Dev, 20:76-80 (2016).

* cited by examiner

Fig. 1

```
BS      ---MELFKYMEKYDYEQLVFCQDEQSGLKAIIAIHDTTLGPALGGTRMWTYENEEAAIED 57
BL      ---MELFRYMEQYDYEQLVFCQDKQSGLKAIIAIHDTTLGPALGGTRMWTYESEEAAIED 57
GS      ---MELFKYMETYDYEQVLFCQDKESGLKAIIAIHDTTLGPALGGTRMWMYNSEEEALED 57
BC      -MTLEIFEYLEKYDYEQVVFCQDKESGLKAIIAIHDTTLGPALGGTRMWTYDSEEAAIED 59
TI      ---MKIFDYMEKYDYEQLVMCQDKESGLKAIICIHVTTLGPALGGMRMWTYASEEEAIED 57
BSph    ---MEIFKYMEKYDYEQLVFCQDEASGLKAIIAIHDTTLGPALGGARMWTYATEENAIED 57
CP      MKYSLNFKEIKIDDYERVIEVTCSKVRLHAIIAIHQTAVGPALGGVRASLYSSFEDACTD 60
              *  ::  ***:::    .   *:***.** *::****** *   * . * *  *

BS      ALRLARGMTYKNAAAGLNLGGGKTVIIG-DPRKDKNEEMFRAFGRYIQGLNGRYITAEDV 116
BL      ALRLARGMTYKNAAAGLNLGGGKTVIIG-DPRKDKNEEMFRAFGRYIQGLNGRYITAEDV 116
GS      ALRLARGMTYKNAAAGLNLGGGKTVIIG-DPRKDKNEAMFRAFGRFIQGLNGRYITAEDV 116
BC      ALRLAKGMTYKNAAAGLNLGGAKTVIIG-DPRKDKSEAMFRALGRYIQGLNGRYITAEDV 118
TI      ALRLGRGMTYKNAAAGLNLGGGKTVIIG-DPRKDKNEAMFRALGRFIQGLNGRYITAEDV 116
BSph    ALRLARGMTYKNAAAGLNLGGGKTVIIG-DPFKDKNEEMFRALGRFIQGLNGRYITAEDV 116
CP      ALRLARGMTYKAIISNTGTGGGKSVIILPQDAPSLTEDMLRAFGQAVNALEGTYICAEDL 120
        ****.:*****   :. . **.*:***  :   . .* *:**:*: ::.*:* ** ***:

BS      GTTVEDMDIIHDETDYVTGISPAFGSSGNPSPVTAYGVYRGMKAAAKAAFGTDSLEGKTI 176
BL      GTTVEDMDIIHDETDFVTGISPAFGSSGNPSPVTAYGVYKGMKAAAKAAFGTDSLEGKTV 176
GS      GTTVADMDIIYQETDYVTGISPEFGSSGNPSPATAYGVYRGMKAAAKEAFGSDSLEGKVV 176
BC      GTTVDDMDIIHEETDFVTGISPSFGSSGNPSPVTAYGVYRGMKAAAKEAFGTDNLEGKVI 178
TI      GTTVEDMDIIHEETRYVTGVSPAFGSSGNPSPVTAYGVYRGMKAAAKEAFGDDSLEGKVV 176
BSph    GTTVTDMDLIHEETNYVTGISPAFGSSGNPSPVTAYGVYRGMKAAAKEAFGTDMLEGRTI 176
CP      GVSINDISIVAEETPYVCGIA---DVSGDPSIYTAHGGFLCIKETAKYLWGSSSLRGKKI 177
        *.:: *:.:: :** :* *::   . **:**  **:* :  :* :**  :* . *.*: :
```

Fig. 1 (continued)

```
BS      AVQGVGNVAYNLCRHLHEEGANLIVTDINKQSVQRAVEDFGARAVDPDDIYSQDCDIYAP 236
BL      AVQGVGNVAYNLCRHLHEEGAKLIVTDINKEAVERAVAEFGARAVDPDDIYSQECDIYAP 236
GS      AVQGVGNVAYHLCRHLHEEGAKLIVTDINKEVVARAVEEFGAKAVDPNDIYGVECDIFAP 236
BC      AVQGVGNVAYHLCKHLHAEGAKLIVTDINKEAVQRAVEEFGASAVEPNEIYGVECDIYAP 238
TI      AVQGVGHVAYELCKHLHNEGAKLIVTDINKENADRAVQEFGAEFVHPDKIYDVECDIFAP 236
BSph    SVQGLGNVAYKLCEYLHNEGAKLVVTDINQAAIDRVVNDFGATAVAPDEIYSQEVDIFSP 236
CP      AIQGIGSVGRRLLQSLFFEGAELYVADVLERAVQDAARLYGATIVPTEEIHALECDIFSP 237
        ::**:* *. .* . *. ***:* *:*: :      ..  :**  * .:.*:  : **::*

BS      CALGATINDDTIKQLKAKVIAGAANNQLKETRHGDQIHEMGIVYAPDYVINAGGVINVAD 296
BL      CALGATINDDTIPQLKAKVIAGAANNQLKETRHGDQIHDMGIVYAPDYVINAGGVINVAD 296
GS      CALGGIINDQTIPQLKAKVIAGSADNQLKEPRHGDIIHEMGIVYAPDYVINAGGVINVAD 296
BC      CALGATVNDETIPQLKAKVIAGSANNQLKEDRHGDIIHEMGIVYAPDYVINAGGVINVAD 298
TI      CALGAIINDETIERLKCKVVAGSANNQLKEERHGKMLEEKGIVYAPDYVINAGGVINVAD 296
BSph    CALGAILNDETIPQLKAKVIAGSANNQLQDSRHGDYLHELGIVYAPDYVINAGGVINVAD 296
CP      CARGNVIRKDNLADLNCKAIVGVANNQLEDSSAGMMLHERGILYGPDYLVNAGGLLNVAA 297
        ** *   :..:.:  *:.*.:.* *:***::    *   :.: **:*.***::****::***

BS      ELYG--YNAERALKKVEGIYGNIERVLEISQRDGIPAYLAADRLAEERIERMRRSRSQFL 354
BL      ELYG--YNSERALKKVEGIYGNIERVLEISKRDRIPTYLAADRLAEERIERMRQSRSQFL 354
GS      ELYG--YNRERAMKKIEQIYDNIEKVFAIAKRDNIPTYVAADRMAEERIETMRKARSPFL 354
BC      ELYG--YNRERALKRVESIYDTIAKVIEISKRDGIATYVAADRLAEERIASLKNSRSTYL 356
TI      ELLG--YNRERAMKKVEGIYDKILKVFEIAKRDGIPSYLAADRMAEERIEMMRKTRSTFL 354
BSph    ELYG--YNRERALKRVDGIYDSIEKIFEISKRDSIPTYVAANRLAEERIARVAKSRSQFL 354
CP      AIEGRVYAPKEVLLKVEELPIVLSKLYNQSKTTGKDLVALSDSFVEDKLLAYTS------ 351
         : *   *  :..: ::: :    : ::    ::          :: :.*:::

BS      QNGHSVLSRR--- 364
BL      QNGHHILSRR--- 364
GS      QNGHHILSRRRAR 367
BC      RNGHDIISRR--- 366
TI      QDQRNLINFNNK- 366
BSph    KNEKNILNGR--- 364
CP      -------------
```

VARIANT POLYPEPTIDES CAPABLE OF AMINATING ALIPHATIC ALPHA KETO ACIDS

RELATED APPLICATION

This application claims the benefit of priority to U.S. Provisional Patent Application Ser. No. 62/059,538, filed Oct. 3, 2014.

SEQUENCE LISTING

The instant application contains a Sequence Listing which has been submitted electronically in ASCII format and is hereby incorporated by reference in its entirety. Said ASCII copy, created on Nov. 25, 2015, is named AVR-036.01 (31941.03601)_SL.txt and is 59,277 bytes in size.

BACKGROUND

Synthesis of (S)-2-aminonon-8-enoic acid has been reported in the literature. Faucher, et al., reported a six step synthetic sequence for (S)-2-aminonon-8-enoic acid, which involves catalytic hydrogenation of an enamine substrate utilizing a DUPHOS ligand system as the key step for introduction of α-amino acid chirality (*Org. Lett.* 2004, 6, 2901-2904). Subsequently, Wang, et al., reported an enzymatic approach for the preparation of (S)-2-aminonon-8-enoic acid using acylase for the selective kinetic hydrolysis of a racemic acetamide substrate, with a theoretical step yield of 50%, in a six-step sequence (*Org. Process Res. Dev.* 2007, 11, 60-63). In 2008, an alternate approach involving a whole-cell catalytic system was disclosed for preparation of enantiomerically enriched (S)-2-aminonon-8-enoic acid from the corresponding hydantoin substrate (WO 2008/067981 A2). Subsequently, a different approach was reported (WO 2010/050516 A1; WO 2008/067981 A2) for (S)-2-aminonon-8-enoic acid, which was also based on selective kinetic hydrolysis of a racemic succinyl amide substrate using an L-succinylase enzyme (amidase), with a theoretical 50% step yield.

Previously disclosed methods are neither efficient nor best suited for the large-scale preparation of (S)-2-aminonon-8-enoic acid, as some of them involve multiple steps, with individual steps within a sequence possessing the limitation of a maximum 50% theoretical step yield. Thus, there is a need in the art for an improved process for preparing (S)-2-aminonon-8-enoic acid.

SUMMARY

The disclosure provides, among other things, polypeptides and enzymatically-active fragments thereof capable of aminating an aliphatic keto acid (e.g., aliphatic 2-keto acids). The enzymatic activity of the polypeptides and fragments exhibits a high level of enantioselectivity for the (S)-enantiomer form of aliphatic amino acids so aminated. The polypeptides and fragments are useful for, e.g., converting 2-oxonon-8-enoic acid, in the presence of an ammonia source, to 2-aminonon-8-enoic acid (LCAA).

Accordingly, in one aspect, the disclosure features a polypeptide comprising the amino acid sequence depicted in SEQ ID NO:2 or 13-18, wherein X is not leucine.

In another aspect, the disclosure features a polypeptide comprising an amino acid sequence that is at least 90% identical to: (i) amino acids 6 to 238 of SEQ ID NO:2; (ii) amino acids 7 to 237 of SEQ ID NO:13; (iii) amino acids 4 to 236 of SEQ ID NO:14; (iv) amino acids 4 to 236 of SEQ ID NO:15; (v) amino acids 4 to 236 of SEQ ID NO:16; (vi) amino acids 4 to 236 of SEQ ID NO:17; or (vii) amino acids 4 to 236 of SEQ ID NO:18, wherein X is not leucine.

In another aspect, the disclosure features a polypeptide comprising an amino acid sequence that is at least 90% identical to: (i) amino acids 6 to 298 of SEQ ID NO:2; (ii) amino acids 7 to 297 of SEQ ID NO:13; (iii) amino acids 4 to 296 of SEQ ID NO:14; (iv) amino acids 4 to 296 of SEQ ID NO:15; (v) amino acids 4 to 296 of SEQ ID NO:16; (vi) amino acids 4 to 296 of SEQ ID NO:17; or (vii) amino acids 4 to 296 of SEQ ID NO:18, wherein X is not leucine.

In another aspect, the disclosure features a polypeptide comprising an amino acid sequence having at least two amino acid substitutions, deletions, or insertions relative to SEQ ID NO:2, wherein the amino acid sequence comprises the amino acid X at position 42, and wherein X is not leucine.

In another aspect, the disclosure features a polypeptide comprising an amino acid sequence having at least two amino acid substitutions, deletions, or insertions relative to SEQ ID NO:13, wherein the amino acid sequence comprises the amino acid X at position 43, and wherein X is not leucine.

In another aspect, the disclosure features a polypeptide comprising an amino acid sequence having at least two amino acid substitutions, deletions, or insertions relative to SEQ ID NO:14, wherein the amino acid sequence comprises the amino acid X at position 40, and wherein X is not leucine.

In another aspect, the disclosure features a polypeptide comprising an amino acid sequence having at least two amino acid substitutions, deletions, or insertions relative to SEQ ID NO:15, wherein the amino acid sequence comprises the amino acid X at position 40, and wherein X is not leucine.

In another aspect, the disclosure features a polypeptide comprising an amino acid sequence having at least two amino acid substitutions, deletions, or insertions relative to SEQ ID NO:16, wherein the amino acid sequence comprises the amino acid X at position 40, and wherein X is not leucine.

In another aspect, the disclosure features a polypeptide comprising an amino acid sequence having at least two amino acid substitutions, deletions, or insertions relative to SEQ ID NO:17, wherein the amino acid sequence comprises the amino acid X at position 40, and wherein X is not leucine.

In another aspect, the disclosure features a polypeptide comprising an amino acid sequence having at least two amino acid substitutions, deletions, or insertions relative to SEQ ID NO:18, wherein the amino acid sequence comprises the amino acid X at position 40, and wherein X is not leucine.

In yet another aspect, the disclosure features a polypeptide comprising the amino acid sequence depicted in SEQ ID NO: 4, 5, 6, or 20.

In yet another aspect, the disclosure features a polypeptide comprising at least ten (e.g., at least 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 or more) consecutive amino acids of SEQ ID NO:2, inclusive of the amino acid at position 42, wherein X is not leucine.

In yet another aspect, the disclosure features a polypeptide comprising at least ten (e.g., at least 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 or more) consecutive amino acids of SEQ ID NO:13, inclusive of the amino acid at position 43, wherein X is not leucine.

In yet another aspect, the disclosure features a polypeptide comprising at least ten (e.g., at least 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 or more) consecutive amino acids of SEQ ID NO:14, inclusive of the amino acid at position 40, wherein X is not leucine.

In yet another aspect, the disclosure features a polypeptide comprising at least ten (e.g., at least 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 or more) consecutive amino acids of SEQ ID NO:15, inclusive of the amino acid at position 40, wherein X is not leucine.

In yet another aspect, the disclosure features a polypeptide comprising at least ten (e.g., at least 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 or more) consecutive amino acids of SEQ ID NO:16, inclusive of the amino acid at position 40, wherein X is not leucine.

In yet another aspect, the disclosure features a polypeptide comprising at least ten (e.g., at least 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 or more) consecutive amino acids of SEQ ID NO:17, inclusive of the amino acid at position 40, wherein X is not leucine.

In yet another aspect, the disclosure features a polypeptide comprising at least ten (e.g., at least 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 or more) consecutive amino acids of SEQ ID NO:18, inclusive of the amino acid at position 40, wherein X is not leucine.

In some embodiments, any of the polypeptides described herein comprise the amino acid sequence: GPAXGG (SEQ ID NO:3), wherein X is not leucine.

In some embodiments, any of the polypeptides described herein comprise at least 50 consecutive amino acids of SEQ ID NO:2. In some embodiments, any of the polypeptides described herein comprise at least 100 consecutive amino acids of SEQ ID NO:2.

In some embodiments, any of the polypeptides described herein have an enzymatic activity that converts 2-oxonon-8-enoic acid to (S)-2-aminonon-8-enoic acid (LCAA). For example, a polypeptide described herein can, in the presence of an ammonia source, convert 2-oxonon-8-enoic acid to (S)-2-aminonon-8-enoic acid (LCAA), e.g., under the assay conditions described herein and exemplified in the working examples. In some embodiments, a polypeptide described herein has an enhanced enzymatic activity to convert 2-oxonon-8-enoic acid to (S)-2-aminonon-8-enoic acid (LCAA), as compared to wild-type, full-length *B. cereus* LDH, e.g., SEQ ID NO:1.

In some embodiments of any of the polypeptides described herein, e.g., SEQ ID NO:2, 3, or any one of 13-18, X is isoleucine. In some embodiments of any of the polypeptides described herein, e.g., SEQ ID NO:2, 3, or any one of 13-18, X is valine. In some embodiments of any of the polypeptides described herein, e.g., SEQ ID NO:2, 3, or 13-18, X is glycine. In some embodiments of any of the polypeptides described herein, e.g., SEQ ID NO:2, 3, or any one of 13-18, X is alanine. In some embodiments of any of the polypeptides described herein, e.g., SEQ ID NO:2, 3, or any one of 13-18, X is serine. In some embodiments of any of the polypeptides described herein, e.g., SEQ ID NO:2, 3, or 13-18, X is threonine. In some embodiments of any of the polypeptides described herein, e.g., SEQ ID NO:2, 3, or 13-18, X can be, e.g., isoleucine, valine, glycine, alanine, serine, or threonine.

In some embodiments, the polypeptides described herein can be isolated polypeptides.

In yet another aspect, the disclosure features a nucleic acid encoding any one or more of the polypeptides described herein. Also featured are expression vectors (e.g., prokaryotic or eukaryotic) expression vectors comprising the nucleic acid. In another aspect, the disclosure features a cell, plurality of cells, or culture of cells, comprising the nucleic acid or expression vector. In another aspect, the disclosure features a method for producing a polypeptide, such as any of the polypeptides described herein. The method includes culturing the aforementioned cell, plurality of cells, or culture of cells comprising the expression vector under conditions suitable for protein expression to thereby produce a polypeptide. The method can, optionally, further include isolating the polypeptide from the cell (plurality of cells or cell culture) or from media in which the cell or cells is/are cultured.

In yet another aspect, the disclosure features a kit comprising any one of the polypeptides described herein. In some embodiments, the kit includes instructions for aminating an aliphatic keto acid. In some embodiments, the kit includes an aliphatic keto acid, one or more reaction buffers, an ammonia source, a glucose dehydrogenase, glucose, nicotinamide adenine dinucleotide (NAD; e.g., a reduced form of NAD), or combinations of any of the foregoing.

"Polypeptide," "peptide," and "protein" are used interchangeably and mean any peptide-linked chain of amino acids, regardless of length or post-translational modification.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for reductive amination of an aliphatic keto acid, will be apparent from the following description, the examples, and from the claims.

BRIEF DESCRIPTION OF THE SEQUENCES

SEQ ID NO:1 is an exemplary amino acid sequence for wild-type *B. cereus* leucine dehydrogenase.

SEQ ID NO:2 is an exemplary amino acid sequence for a variant *B. cereus* leucine dehydrogenase (substitution X at position 42).

SEQ ID NO:3 is a six amino acid conserved region from bacterial leucine dehydrogenase polypeptides.

SEQ ID NO:4 depicts an exemplary amino acid sequence for the variant *B. cereus* LDH-L42I polypeptide.

SEQ ID NO:5 depicts an exemplary amino acid sequence for the variant *B. cereus* LDH-L42V polypeptide.

SEQ ID NO:6 depicts an exemplary amino acid sequence for the variant *B. cereus* LDH-L42G polypeptide.

SEQ ID NO:7 is an exemplary amino acid sequence for wild-type *Chlamydia pneumoniae* leucine dehydrogenase.

SEQ ID NO:8 is an exemplary amino acid sequence for wild-type *Thermoactinomyces intermedius* leucine dehydrogenase.

SEQ ID NO:9 is an exemplary amino acid sequence for wild-type *Bacillus subtilis* leucine dehydrogenase.

SEQ ID NO:10 is an exemplary amino acid sequence for wild-type *Bacillus licheniformis* leucine dehydrogenase.

SEQ ID NO:11 is an exemplary amino acid sequence for wild-type *Geobacillus stearothermophilus* leucine dehydrogenase.

SEQ ID NO:12 is an exemplary amino acid sequence for wild-type *Bacillus sphaericus* leucine dehydrogenase.

SEQ ID NO:13 is an exemplary amino acid sequence for a variant *Chlamydia pneumoniae* leucine dehydrogenase (substitution X at position 43).

SEQ ID NO:14 is an exemplary amino acid sequence for a variant *Thermoactinomyces intermedius* leucine dehydrogenase (substitution X at position 40).

SEQ ID NO:15 is an exemplary amino acid sequence for a variant *Bacillus subtilis* leucine dehydrogenase (substitution X at position 40).

SEQ ID NO:16 is an exemplary amino acid sequence for a variant *Bacillus licheniformis* leucine dehydrogenase (substitution X at position 40).

SEQ ID NO:17 is an exemplary amino acid sequence for a variant *Geobacillus stearothermophilus* leucine dehydrogenase (substitution X at position 40).

SEQ ID NO:18 is an exemplary amino acid sequence for a variant *Bacillus sphaericus* leucine dehydrogenase (substitution X at position 40).

SEQ ID NO:19 is a three amino acid conserved region from bacterial leucine dehydrogenase polypeptides.

SEQ ID NO:20 depicts an exemplary amino acid sequence for the variant *B. cereus* LDH-L42A polypeptide.

BRIEF DESCRIPTION OF THE DRAWINGS

FIG. 1 depicts the alignment of the amino acid sequences of leucine dehydrogenases from *Bacillus cereus* (BC) (SEQ ID NO:1), *Chlamydia pneumoniae* (CP) (SEQ ID NO:7), *Thermoactinomyces intermedius* (TI) (SEQ ID NO:8), *Bacillus subtilis* (BS) (SEQ ID NO:9), *Bacillus licheniformis* (BL) (SEQ ID NO:10), *Geobacillus stearothermophilus* (GS) (SEQ ID NO:11), and *Bacillus sphaericus* (BSph) (SEQ ID NO:12). Sequence identity is indicated by "*". Sequence conservation (e.g., conservative substitutions) between species is indicated by ":". The alignment was performed using the ClustalW2™ software provided by the European Bioinformatics Institute (EBI) of the European Molecular Biology Laboratory (EMBL).

DETAILED DESCRIPTION

Figure 2:
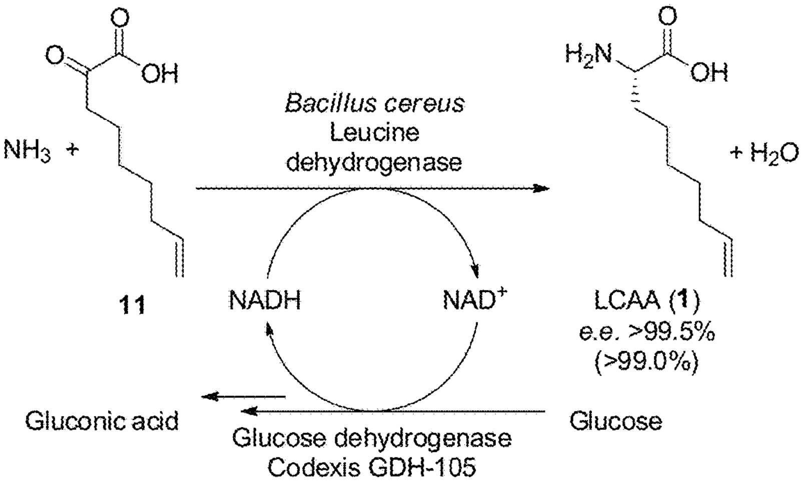
FIG. 2 depicts a reaction scheme for converting 2-oxonon-8-enoic acid, in the presence of an ammonia source, to 2-aminonon-8-enoic acid (LCAA). Also depicted, in conjunction with the amination reaction, are glucose dehydrogenase (GDH) and glucose, which are used to regenerate a catalytic amount of the NADH cofactor.

The disclosure relates to, among other things, polypeptides (e.g., variant polypeptides and enzymatically-active fragments thereof), nucleic acids encoding the polypeptides, production of the polypeptides, and use of the polypeptides in various applications, such as screening and synthetic methods. For example, the variant polypeptides, or enzymatically-active fragments thereof, are useful for converting aliphatic keto acids to aliphatic alpha amino acids. While in no way intended to be limiting, exemplary variant polypeptides, fragments, and methods for making and using any of the foregoing are elaborated on below.

Polypeptides

The polypeptides described herein include variants of leucine dehydrogenase (LDH) and enzymatically-active fragments of such variants. In some embodiments, the polypeptide is a variant of a LDH expressed by *Bacillus cereus*, or an enzymatically-active fragment of the variant. An exemplary amino acid sequence for the full-length, wild-type LDH polypeptide from *Bacillus cereus* is as follows:

```
                                          (SEQ ID NO: 1)
MTLEIFEYLEKYDYEQVVFCQDKESGLKAIIAIHDTTLGPALGGTRMWTY

DSEEAAIEDALRLAKGMTYKNAAAGLNLGGAKTVIIGDPRKDKSEAMFRA

LGRYIQGLNGRYITAEDVGTTVDDMDIIHEETDFVTGISPSFGSSGNPSP

VTAYGVYRGMKAAAKEAFGTDNLEGKVIAVQGVGNVAYHLCKHLHAEGAK

LIVTDINKEAVQRAVEEFGASAVEPNEIYGVECDIYAPCALGATVNDETI

PQLKAKVIAGSANNQLKEDRHGDIIHEMGIVYAPDYVINAGGVINVADEL

YGYNRERALKRVESIYDTIAKVIEISKRDGIATYVAADRLAEERIASLKN

SRSTYLRNGHDIISRR (UniProt ID No. P0A392).
```

In some embodiments, the polypeptide is a variant of a LDH expressed by *Chlamydia pneumoniae*, or an enzymatically-active fragment of the variant. An exemplary amino acid sequence for the full-length, wild-type LDH polypeptide from *Chlamydia pneumoniae* is as follows:

```
                                          (SEQ ID NO: 7)
MKYSLNFKEIKIDDYERVIEVTCSKVRLHAIIAIHQTAVGPALGGVRASL

YSSFEDACTDALRLARGMTYKAIISNTGTGGGKSVIILPQDAPSLTEDML

RAFGQAVNALEGTYICAEDLGVSINDISIVAEETPYVCGIADVSGDPSIY

TAHGGFLCIKETAKYLWGSSSLRGKKIAIQGIGSVGRRLLQSLFFEGAEL

YVADVLERAVQDAARLYGATIVPTEEIHALECDIFSPCARGNVIRKDNLA

DLNCKAIVGVANNQLEDSSAGMMLHERGILYGPDYLVNAGGLLNVAAAIE

GRVYAPKEVLLKVEELPIVLSKLYNQSKTTGKDLVALSDSFVEDKLLAYT

S (UniProt ID No. Q9Z6Y7).
```

In some embodiments, the polypeptide is a variant of a LDH expressed by *Thermoactinomyces intermedius*, or an enzymatically-active fragment of the variant. An exemplary amino acid sequence for the full-length, wild-type LDH polypeptide from *Thermoactinomyces intermedius* is as follows:

```
                                        (SEQ ID NO: 8)
MKIFDYMEKYDYEQLVMCQDKESGLKAIICIHVTTLGPALGGMRMWTYAS

EEEAIEDALRLGRGMTYKNAAAGLNLGGGKTVIIGDPRKDKNEAMFRALG

RFIQGLNGRYITAEDVGTTVEDMDIIHEETRYVTGVSPAFGSSGNPSPVT

AYGVYRGMKAAAKEAFGDDSLEGKVVAVQGVGHVAYELCKHLHNEGAKLI

VTDINKENADRAVQEFGAEFVHPDKIYDVECDIFAPCALGAIINDETIER

LKCKVVAGSANNQLKEERHGKMLEEKGIVYAPDYVINAGGVINVADELLG

YNRERAMKKVEGIYDKILKVFEIAKRDGIPSYLAADRMAEERIEMMRKTR

STFLQDQRNLINFNNK (UniProt ID No. Q60030).
```

In some embodiments, the polypeptide is a variant of a LDH expressed by *Bacillus subtilis*, or an enzymatically-active fragment of the variant. An exemplary amino acid sequence for the full-length, wild-type LDH polypeptide from *Bacillus subtilis* is as follows:

```
                                        (SEQ ID NO: 9)
MELFKYMEKYDYEQLVFCQDEQSGLKAIIAIHDTTLGPALGGTRMWTYEN

EEAAIEDALRLARGMTYKNAAAGLNLGGGKTVIIGDPRKDKNEEMFRAFG

RYIQGLNGRYITAEDVGTTVEDMDIIHDETDYVTGISPAFGSSGNPSPVT

AYGVYRGMKAAAKAAFGTDSLEGKTIAVQGVGNVAYNLCRHLHEEGANLI

VTDINKQSVQRAVEDFGARAVDPDDIYSQDCDIYAPCALGATINDDTIKQ

LKAKVIAGAANNQLKETRHGDQIHEMGIVYAPDYVINAGGVINVADELYG

YNAERALKKVEGIYGNIERVLEISQRDGIPAYLAADRLAEERIERMRRSR

SQFLQNGHSVLSRR (UniProt ID No. P54531).
```

In some embodiments, the polypeptide is a variant of a LDH expressed by *Bacillus licheniformis*, or an enzymatically-active fragment of the variant. An exemplary amino acid sequence for the full-length, wild-type LDH polypeptide from *Bacillus licheniformis* is as follows:

```
                                        (SEQ ID NO: 10)
MELFRYMEQYDYEQLVFCQDKQSGLKAIIAIHDTTLGPALGGTRMWTYES

EEAAIEDALRLARGMTYKNAAAGLNLGGGKTVIIGDPRKDKNEEMFRAFG

RYIQGLNGRYITAEDVGTTVEDMDIIHDETDFVTGISPAFGSSGNPSPVT

AYGVYKGMKAAAKAAFGTDSLEGKTVAVQGVGNVAYNLCRHLHEEGAKLI

VTDINKEAVERAVAEFGARAVDPDDIYSQECDIYAPCALGATINDDTIPQ

LKAKVIAGAANNQLKETRHGDQIHDMGIVYAPDYVINAGGVINVADELYG

YNSERALKKVEGIYGNIERVLEISKRDRIPTYLAADRLAEERIERMRQSR

SQFLQNGHHILSRR (UniProt ID No. Q65HK5).
```

In some embodiments, the polypeptide is a variant of a LDH expressed by *Geobacillus stearothermophilus*, or an enzymatically-active fragment of the variant. An exemplary amino acid sequence for the full-length, wild-type LDH polypeptide from *Geobacillus stearothermophilus* is as follows:

```
                                        (SEQ ID NO: 11)
MELFKYMETYDYEQVLFCQDKESGLKAIIAIHDTTLGPALGGTRMWMYNS

EEEALEDALRLARGMTYKNAAAGLNLGGGKTVIIGDPRKDKNEAMFRAFG

RFIQGLNGRYITAEDVGTTVADMDIIYQETDYVTGISPEFGSSGNPSPAT

AYGVYRGMKAAAKEAFGSDSLEGKVVAVQGVGNVAYHLCRHLHEEGAKLI

VTDINKEVVARAVEEFGAKAVDPNDIYGVECDIFAPCALGGIINDQTIPQ

LKAKVIAGSADNQLKEPRHGDIIHEMGIVYAPDYVINAGGVINVADELYG

YNRERAMKKIEQIYDNIEKVFAIAKRDNIPTYVAADRMAEERIETMRKAR

SPFLQNGHHILSRRRAR (UniProt ID No. P13154).
```

In some embodiments, the polypeptide is a variant of a LDH expressed by *Bacillus sphaericus*, or an enzymatically-active fragment of the variant. An exemplary amino acid sequence for the full-length, wild-type LDH polypeptide from *Bacillus sphaericus* is as follows:

```
                                        (SEQ ID NO: 12)
MEIFKYMEKYDYEQLVFCQDEASGLKAIIAIHDTTLGPALGGARMWTYAT

EENAIEDALRLARGMTYKNAAAGLNLGGGKTVIIGDPFKDKNEEMFRALG

RFIQGLNGRYITAEDVGTTVTDMDLIHEETNYVTGISPAFGSSGNPSPVT

AYGVYRGMKAAAKEAFGTDMLEGRTISVQGLGNVAYKLCEYLHNEGAKLV

VTDINQAAIDRVVNDFGATAVAPDEIYSQEVDIFSPCALGAILNDETIPQ

LKAKVIAGSANNQLQDSRHGDYLHELGIVYAPDYVINAGGVINVADELYG

YNRERALKRVDGIYDSIEKIFEISKRDSIPTYVAANRLAEERIARVAKSR

SQFLKNEKNILNGR (UniProt ID No. Q76GS2).
```

The variant polypeptides described herein comprise one or more amino acid substitutions, insertions, or deletions, relative to the wild-type LDH polypeptides from which they were derived. In some embodiments, a variant polypeptide comprises at least two (e.g., at least three, four, five, six, seven, eight, nine, 10, 15, 20, 25, 30, 35, 40, 45, 50, 55, 60, 65, 70, 75, 80, 85, 90, 95, 100, or more than 100) amino acid substitutions, deletions, or insertions, relative to the wild-type, full-length LDH polypeptide from which it was derived. In some embodiments, a variant polypeptide comprises no more than 150 (e.g., no more than 145, 140, 135, 130, 125, 120, 115, 110, 105, 100, 95, 90, 85, 80, 75, 70, 65, 60, 55, 50, 45, 40, 35, 30, 25, 24, 23, 22, 21, 20, 19, 18, 17, 16, 15, 14, 13, 12, 11, 10, 9, 8, 7, 6, 5, 4, 3, or 2) amino acid substitutions, deletions, or insertions, relative to the wild-type, full-length LDH polypeptide from which it was derived. In some embodiments, a variant polypeptide described herein, or a fragment thereof, includes an amino acid substitution at amino acid position 42 relative to SEQ ID NO:1, e.g., a substitution of leucine at position 42 with another amino acid. The amino acid at position 42, leucine, relative to SEQ ID NO:1 is one of several amino acids (GPAXGG (SEQ ID NO:3)) highly conserved among bacterial leucine dehydrogenase polypeptides (FIG. 1). However, the exact position of these amino acid residues in a given polypeptide varies from species to species and with truncations or extension of the naturally-occurring sequence. One of skill in the art would therefore appreciate that references herein to a variant polypeptide (or a fragment thereof) comprising an amino acid substitution at position 42 relative to SEQ ID NO:1, include, e.g., an amino acid substitution at position 43 of SEQ ID NO:7; an amino acid substitution at position 40 of SEQ ID NO:8; an amino acid substitution at position 40 of SEQ ID NO:9; an amino acid substitution at position 40 of SEQ ID NO:10; an amino acid substitution at position 40 of SEQ ID NO:11; or an amino acid substitution at position 40 of SEQ ID NO:12, i.e., position X in SEQ ID NOs:13-18.

In some embodiments, any of the variant polypeptides or fragments described herein comprise the amino acid sequence NVA (SEQ ID NO:19), which corresponds to amino acids 295 to 297 of SEQ ID NO:1. In some embodiments, a variant polypeptide or fragment thereof comprises the amino acid sequences depicted in SEQ ID NO:3 and SEQ ID NO:19.

As used herein, the term "conservative substitution" refers to the replacement of an amino acid present in the native sequence in a given polypeptide with a naturally or non-naturally occurring amino acid having similar steric properties. Where the side-chain of the native amino acid to be replaced is either polar or hydrophobic, the conservative substitution should be with a naturally occurring amino acid, a non-naturally occurring amino acid that is also polar or hydrophobic, and, optionally, with the same or similar steric properties as the side-chain of the replaced amino acid. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. One letter amino acid abbreviations are as follows: alanine (A); arginine (R); asparagine (N); aspartic acid (D); cysteine (C); glycine (G); glutamine (Q); glutamic acid (E); histidine (H); isoleucine (I); leucine (L); lysine (K); methionine (M); phenylalanine (F); proline (P); serine (S); threonine (T); tryptophan (W), tyrosine (Y); and valine (V).

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted.

In some embodiments, the variant polypeptide, or fragment thereof, comprises the amino acid sequence GPAXGG (SEQ ID NO:3), wherein X is any amino acid except for leucine. In some embodiments, X is glycine. In some embodiments, X is valine. In some embodiments, X is isoleucine. In some embodiments, X is alanine. In some embodiments, X is serine. In some embodiments, X is threonine. In some embodiments, X can be, e.g., glycine, valine, isoleucine, alanine, serine, or threonine.

In some embodiments, the variant polypeptide is a variant of *Bacillus cereus* LDH comprising the following amino acid sequence:

```
                                        (SEQ ID NO: 2)
MTLEIFEYLEKYDYEQVVFCQDKESGLKAIIAIHDTTLGPAXGGTRMWTY

DSEEAAIEDALRLAKGMTYKNAAAGLNLGGAKTVIIGDPRKDKSEAMFRA

LGRYIQGLNGRYITAEDVGTTVDDMDIIHEETDFVTGISPSFGSSGNPSP
```

-continued

```
VTAYGVYRGMKAAAKEAFGTDNLEGKVIAVQGVGNVAYHLCKHLHAEGAK

LIVTDINKEAVQRAVEEFGASAVEPNEIYGVECDIYAPCALGATVNDETI

PQLKAKVIAGSANNQLKEDRHGDIIHEMGIVYAPDYVINAGGVINVADEL

YGYNRERALKRVESIYDTIAKVIEISKRDGIATYVAADRLAEERIASLKN

SRSTYLRNGHDIISRR,
```

wherein X is any amino acid except for leucine. In some embodiments, X is glycine. In some embodiments, X is valine. In some embodiments, X is isoleucine. In some embodiments, X is alanine. In some embodiments, X is serine. In some embodiments, X is threonine. In some embodiments, X can be, e.g., glycine, valine, isoleucine, alanine, serine, or threonine.

In some embodiments, the variant polypeptide comprises, or consists of, one of the following amino acid sequences:

```
(1)
                                        (SEQ ID NO: 4)
MTLEIFEYLEKYDYEQVVFCQDKESGLKAIIAIHDTTLGPAIGGTRMWTY

DSEEAAIEDALRLAKGMTYKNAAAGLNLGGAKTVIIGDPRKDKSEAMFRA

LGRYIQGLNGRYITAEDVGTTVDDMDIIHEETDFVTGISPSFGSSGNPSP

VTAYGVYRGMKAAAKEAFGTDNLEGKVIAVQGVGNVAYHLCKHLHAEGAK

LIVTDINKEAVQRAVEEFGASAVEPNEIYGVECDIYAPCALGATVNDETI

PQLKAKVIAGSANNQLKEDRHGDIIHEMGIVYAPDYVINAGGVINVADEL

YGYNRERALKRVESIYDTIAKVIEISKRDGIATYVAADRLAEERIASLKN

SRSTYLRNGHDIISRR;

(2)
                                        (SEQ ID NO: 5)
MTLEIFEYLEKYDYEQVVFCQDKESGLKAIIAIHDTTLGPAVGGTRMWTY

DSEEAAIEDALRLAKGMTYKNAAAGLNLGGAKTVIIGDPRKDKSEAMFRA

LGRYIQGLNGRYITAEDVGTTVDDMDIIHEETDFVTGISPSFGSSGNPSP

VTAYGVYRGMKAAAKEAFGTDNLEGKVIAVQGVGNVAYHLCKHLHAEGAK

LIVTDINKEAVQRAVEEFGASAVEPNEIYGVECDIYAPCALGATVNDETI

PQLKAKVIAGSANNQLKEDRHGDIIHEMGIVYAPDYVINAGGVINVADEL

YGYNRERALKRVESIYDTIAKVIEISKRDGIATYVAADRLAEERIASLKN

SRSTYLRNGHDIISRR;

(3)
                                        (SEQ ID NO: 6)
MTLEIFEYLEKYDYEQVVFCQDKESGLKAIIAIHDTTLGPAGGGTRMWTY

DSEEAAIEDALRLAKGMTYKNAAAGLNLGGAKTVIIGDPRKDKSEAMFRA

LGRYIQGLNGRYITAEDVGTTVDDMDIIHEETDFVTGISPSFGSSGNPSP

VTAYGVYRGMKAAAKEAFGTDNLEGKVIAVQGVGNVAYHLCKHLHAEGAK

LIVTDINKEAVQRAVEEFGASAVEPNEIYGVECDIYAPCALGATVNDETI

PQLKAKVIAGSANNQLKEDRHGDIIHEMGIVYAPDYVINAGGVINVADEL

YGYNRERALKRVESIYDTIAKVIEISKRDGIATYVAADRLAEERIASLKN

SRSTYLRNGHDIISRR;
or
```

-continued (4)

(SEQ ID NO: 20)

```
MTLEIFEYLEKYDYEQVVFCQDKESGLKAIIAIHDTTLGPAAGGTRMWTY
DSEEAAIEDALRLAKGMTYKNAAAGLNLGGAKTVIIGDPRKDKSEAMFRA
LGRYIQGLNGRYITAEDVGTTVDDMDIIHEETDFVTGISPSFGSSGNPSP
VTAYGVYRGMKAAAKEAFGTDNLEGKVIAVQGVGNVAYHLCKHLHAEGAK
LIVTDINKEAVQRAVEEFGASAVEPNEIYGVECDIYAPCALGATVNDETI
PQLKAKVIAGSANNQLKEDRHGDIIHEMGIVYAPDYVINAGGVINVADEL
YGYNRERALKRVESIYDTIAKVIEISKRDGIATYVAADRLAEERIASLKN
SRSTYLRNGHDIISRR.
```

In some embodiments, a variant polypeptide described herein, or a fragment thereof, comprises at least ten (e.g., at least 11, 12, 13, 14, 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, or 300 or more) consecutive amino acids of SEQ ID NO:2, inclusive of the amino acid at position 42, wherein X is not leucine.

In some embodiments, a variant polypeptide described herein, or a fragment thereof, comprises at least ten (e.g., at least 11, 12, 13, 14, 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, or 300 or more) consecutive amino acids of SEQ ID NO:13, inclusive of the amino acid at position 43, wherein X is not leucine. The amino acid sequence of SEQ ID NO:13 is as follows:

```
MKYSLNFKEIKIDDYERVIEVTCSKVRLHAIIAIHQTAVGPAXGGVRASL
YSSFEDACTDALRLARGMTYKAIISNTGTGGGKSVIILPQDAPSLTEDML
RAFGQAVNALEGTYICAEDLGVSINDISIVAEETPYVCGIADVSGDPSIY
TAHGGFLCIKETAKYLWGSSSLRGKKIAIQGIGSVGRRLLQSLFFEGAEL
YVADVLERAVQDAARLYGATIVPTEEIHALECDIFSPCARGNVIRKDNLA
DLNCKAIVGVANNQLEDSSAGMMLHERGILYGPDYLVNAGGLLNVAAAIE
GRVYAPKEVLLKVEELPIVLSKLYNQSKTTGKDLVALSDSFVEDKLLAYT
S.
```

In some embodiments, a variant polypeptide described herein, or a fragment thereof, comprises at least ten (e.g., at least 11, 12, 13, 14, 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, or 300 or more) consecutive amino acids of SEQ ID NO:14, inclusive of the amino acid at position 40, wherein X is not leucine. The amino acid sequence of SEQ ID NO:14 is as follows:

```
MKIFDYMEKYDYEQLVMCQDKESGLKAIICIHVTTLGPAXGGMRMWTYAS
EEEAIEDALRLGRGMTYKNAAAGLNLGGGKTVIIGDPRKDKNEAMFRALG
RFIQGLNGRYITAEDVGTTVEDMDIIHEETRYVTGVSPAFGSSGNPSPVT
AYGVYRGMKAAAKEAFGDDSLEGKVVAVQGVGHVAYELCKHLHNEGAKLI
VTDINKENADRAVQEFGAEFVHPDKIYDVECDIFAPCALGAIINDETIER
```

-continued

```
LKCKVVAGSANNQLKEERHGKMLEEKGIVYAPDYVINAGGVINVADELLG
YNRERAMKKVEGIYDKILKVFEIAKRDGIPSYLAADRMAEERIEMMRKTR
STFLQDQRNLINFNNK.
```

In some embodiments, a variant polypeptide described herein, or a fragment thereof, comprises at least ten (e.g., at least 11, 12, 13, 14, 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, or 300 or more) consecutive amino acids of SEQ ID NO:15, inclusive of the amino acid at position 40, wherein X is not leucine. The amino acid sequence of SEQ ID NO:15 is as follows:

```
MELFKYMEKYDYEQLVFCQDEQSGLKAIIAIHDTTLGPAXGGTRMWTYEN
EEAAIEDALRLARGMTYKNAAAGLNLGGGKTVIIGDPRKDKNEEMFRAFG
RYIQGLNGRYITAEDVGTTVEDMDIIHDETDYVTGISPAFGSSGNPSPVT
AYGVYRGMKAAAKAAFGTDSLEGKTIAVQGVGNVAYNLCRHLHEEGANLI
VTDINKQSVQRAVEDFGARAVDPDDIYSQDCDIYAPCALGATINDDTIKQ
LKAKVIAGAANNQLKETRHGDQIHEMGIVYAPDYVINAGGVINVADELYG
YNAERALKKVEGIYGNIERVLEISQRDGIPAYLAADRLAEERIERMRRSR
SQFLQNGHSVLSRR.
```

In some embodiments, a variant polypeptide described herein, or a fragment thereof, comprises at least ten (e.g., at least 11, 12, 13, 14, 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, or 300 or more) consecutive amino acids of SEQ ID NO:16, inclusive of the amino acid at position 40, wherein X is not leucine. The amino acid sequence of SEQ ID NO:16 is as follows:

```
MELFRYMEQYDYEQLVFCQDKQSGLKAIIAIHDTTLGPAXGGTRMWTYES
EEAAIEDALRLARGMTYKNAAAGLNLGGGKTVIIGDPRKDKNEEMFRAFG
RYIQGLNGRYITAEDVGTTVEDMDIIHDETDFVTGISPAFGSSGNPSPVT
AYGVYKGMKAAAKAAFGTDSLEGKTVAVQGVGNVAYNLCRHLHEEGAKLI
VTDINKEAVERAVAEFGARAVDPDDIYSQECDIYAPCALGATINDDTIPQ
LKAKVIAGAANNQLKETRHGDQIHDMGIVYAPDYVINAGGVINVADELYG
YNSERALKKVEGIYGNIERVLEISKRDRIPTYLAADRLAEERIERMRQSR
SQFLQNGHHILSRR.
```

In some embodiments, a variant polypeptide described herein, or a fragment thereof, comprises at least ten (e.g., at least 11, 12, 13, 14, 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, or 300 or more) consecutive amino acids of SEQ ID NO:17, inclusive of the amino acid at position 40, wherein X is not leucine. The amino acid sequence of SEQ ID NO:17 is as follows:

MELFKYMETYDYEQVLFCQDKESGLKAIIAIHDTTLGPAXGGTRMWMYNS

EEEALEDALRLARGMTYKNAAAGLNLGGGKTVIIGDPRKDKNEAMFRAFG

RFIQGLNGRYITAEDVGTTVADMDIIYQETDYVTGISPEFGSSGNPSPAT

AYGVYRGMKAAAKEAFGSDSLEGKVVAVQGVGNVAYHLCRHLHEEGAKLI

VTDINKEVVARAVEEFGAKAVDPNDIYGVECDIFAPCALGGIINDQTIPQ

LKAKVIAGSADNQLKEPRHGDIIHEMGIVYAPDYVINAGGVINVADELYG

YNRERAMKKIEQIYDNIEKVFAIAKRDNIPTYVAADRMAEERIETMRKAR

SPFLQNGHHILSRRRAR.

In some embodiments, a variant polypeptide described herein, or a fragment thereof, comprises at least 10 (e.g., at least 11, 12, 13, 14, 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, or 300 or more) consecutive amino acids of SEQ ID NO:18, inclusive of the amino acid at position 40, wherein X is not leucine. The amino acid sequence of SEQ ID NO:18 is as follows:

MEIFKYMEKYDYEQLVFCQDEASGLKAIIAIHDTTLGPAXGGARMWTYAT

EENAIEDALRLARGMTYKNAAAGLNLGGGKTVIIGDPFKDKNEEMFRALG

RFIQGLNGRYITAEDVGTTVTDMDLIHEETNYVTGISPAFGSSGNPSPVT

AYGVYRGMKAAAKEAFGTDMLEGRTISVQGLGNVAYKLCEYLHNEGAKLV

VTDINQAAIDRVVNDFGATAVAPDEIYSQEVDIFSPCALGAILNDETIPQ

LKAKVIAGSANNQLQDSRHGDYLHELGIVYAPDYVINAGGVINVADELYG

YNRERALKRVDGIYDSIEKIFEISKRDSIPTYVAANRLAEERIARVAKSR

SQFLKNEKNILNGR.

In some embodiments of any of the variants described herein, X is glycine, isoleucine, alanine, or valine. In some embodiments, X is serine. In some embodiments, X is threonine. In some embodiments, X can be, e.g., glycine, valine, isoleucine, alanine, serine, and threonine.

In some embodiments, a variant polypeptide described herein, or a fragment thereof, has an amino acid sequence that is at least 80 (e.g., at least 81, 82, 83, 84, 85, 86, 87, 88, 89, 90, 91, 92, 93, 94, 95, 96, 97, 98, or 99) % identical to: (i) amino acids 6 to 238 of SEQ ID NO:2; (ii) amino acids 7 to 237 of SEQ ID NO:13; (iii) amino acids 4 to 236 of SEQ ID NO:14; (iv) amino acids 4 to 236 of SEQ ID NO:15; (v) amino acids 4 to 236 of SEQ ID NO:16; (vi) amino acids 4 to 236 of SEQ ID NO:17; or (vii) amino acids 4 to 236 of SEQ ID NO:18, with the proviso that the variant polypeptide or fragment thereof comprises the amino acid sequence at position X, and X is not leucine. In some embodiments, the variant polypeptide or fragment thereof comprises the amino acid sequence depicted in SEQ ID NO:3, wherein X is not leucine.

In some embodiments, a variant polypeptide described herein, or a fragment thereof, has an amino acid sequence that is at least 80 (e.g., at least 81, 82, 83, 84, 85, 86, 87, 88, 89, 90, 91, 92, 93, 94, 95, 96, 97, 98, or 99) % identical to: (i) amino acids 6 to 298 of SEQ ID NO:2; (ii) amino acids 7 to 297 of SEQ ID NO:13; (iii) amino acids 4 to 296 of SEQ ID NO:14; (iv) amino acids 4 to 296 of SEQ ID NO:15; (v) amino acids 4 to 296 of SEQ ID NO:16; (vi) amino acids 4 to 296 of SEQ ID NO:17; or (vii) amino acids 4 to 296 of SEQ ID NO:18, with the proviso that the variant polypeptide or fragment thereof comprises the amino acid sequence at position X, and X is not leucine. In some embodiments, the variant polypeptide or fragment thereof comprises the amino acid sequence depicted in SEQ ID NO:3, wherein X is not leucine.

Percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software, such as BLAST software or ClustalW2 (above). Appropriate parameters for measuring alignment, including any algorithms needed to achieve maximal alignment over the full-length of the sequences being compared can be determined by known methods.

Leucine dehydrogenase from *B. cereus* exists in solution as a homo-octomer, with each subunit folding into two domains, and separated by a deep cleft. See Baker et al. (1995) *Current Biol* 3:693-705, which describes the crystal structure of leucine dehydrogenase from *B. sphaericus* (SEQ ID NO:12). The quaternary structure of the complex adopts the shape of a hollow cylinder. Leucine dehydrogenase comprises both a dehydrogenase superfamily domain (e.g., amino acids 10 to 130) and a nicotinamide adenine dinucleotide-cofactor binding domain (e.g., amino acids 150 to 350). In some embodiments, a variant polypeptide or enzymatically-active fragment described herein retains at least 5 (e.g., at least 10, 15, 20, 25, 30, 35, 40, 45, 50, 55, 60, 65, 70, 75, 80, 85, 90, 95, or 100) % of the ability of the corresponding full-length, wild-type LDH polypeptide from which the variant or fragment was derived to bind to a nucleotide cofactor (e.g., NAD or NADH). Methods for detecting or measuring the interaction between NAD and NAD-dependent enzymes are known in the art and described in, e.g., Kovar and Klukanova (1984) *Biochim Biophys Acta* 788(1):98-109, and Lesk (1995) *Curr Opin Struct Biol* 5(6):775-783.

As described above, the variant polypeptides described herein, as well as enzymatically-active fragments thereof, possess an enzymatic activity capable of reductive amination of an aliphatic keto acid (e.g., aliphatic 2-keto acids). For example, such polypeptides can convert 2-oxonon-8-enoic acid, in the presence of an ammonia source, to LCAA, e.g., (S)-LCAA. In some embodiments, a variant polypeptide, or enzymatically-active fragment thereof, retains at least 5 (e.g., at least 10, 15, 20, 25, 30, 35, 40, 45, 50, 55, 60, 65, 70, 75, 80, 85, 90, 95, or 100) % of the ability of the corresponding full-length, wild-type LDH polypeptide from which the variant or fragment was derived to convert 2-oxonon-8-enoic acid, in the presence of an ammonia source, to LCAA. In some embodiments, a variant polypeptide, or enzymatically-active fragment thereof, retains at least 5 (e.g., at least 10, 15, 20, 25, 30, 35, 40, 45, 50, 55, 60, 65, 70, 75, 80, 85, 90, 95, or 100) % of the ability of full-length, wild-type *Bacillus cereus* LDH octomer complex to convert 2-oxonon-8-enoic acid, in the presence of an ammonia source, to LCAA, e.g., under the assay conditions described and exemplified in the working examples.

In some embodiments, a variant polypeptide, or enzymatically-active fragment thereof, possesses enhanced ability to convert 2-oxonon-8-enoic acid, in the presence of an ammonia source, to LCAA, relative to the activity of full-length, wild-type *Bacillus cereus* LDH. For example, the variant polypeptide or enzymatically-active fragment thereof can have at least a 5 (e.g., 10, 15, 20, 25, 30, 35, 40, 45, 50, 55, 60, 65, 70, 75, 80, 85, 90, 95, or 100) % greater activity (e.g., reaction rate) than full-length, wild-type *Bacillus cereus* LDH to convert 2-oxonon-8-enoic acid, in the presence of an ammonia source, to LCAA. In some embodiments, the activity (e.g., the reaction rate) of the variant polypeptide or enzymatically-active fragment thereof is at least 1.5 (e.g., at least 2, 2.5, 3, 4, 5, 6, 7, 8, 9, 10, 20, 30, 40, 50, 100, 150, 200, 500, or even 1000) times greater than that of full-length, wild-type *Bacillus cereus* LDH, e.g., under the conditions described and exemplified in the working examples. Exemplary variant polypeptides exhibiting enhanced activity relative to full-length, wild-type *B. cereus* LDH include the L42I, L42V, L42G, and L32A variant polypeptides having amino acid sequences: SEQ ID NOs:4, 5, 6, and 20, respectively (see Example 2).

Recombinant Protein Expression and Purification

The variant polypeptides (or fragments) described herein can be produced using a variety of techniques known in the art of molecular biology and protein chemistry. (See, e.g., Current Protocols in Molecular Biology, Wiley & Sons, and Molecular Cloning—A Laboratory Manual—3rd Ed., Cold Spring Harbor Laboratory Press, New York (2001)). For example, a nucleic acid encoding the variant polypeptide or fragment can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification. In addition, the choice of codons, suitable expression vectors and suitable host cells will vary depending on a number of factors, and may be easily optimized as needed.

The variant polypeptides or fragments thereof can be produced from the cells by culturing a host cell transformed with the expression vector containing nucleic acid encoding the proteins or fragments, under conditions, and for an amount of time, sufficient to allow expression of the proteins. Such conditions for protein expression will vary with the choice of the expression vector and the host cell, and will be easily ascertained by one skilled in the art through routine experimentation. For example, proteins expressed in *E. coli* can be refolded from inclusion bodies (see, e.g., Hou et al. (1998) *Cytokine* 10:319-30). Bacterial expression systems and methods for their use are well known in the art (see *Current Protocols in Molecular Biology*, Wiley & Sons, and Molecular Cloning—A Laboratory Manual—3rd Ed., Cold Spring Harbor Laboratory Press, New York (2001), supra).

A number of expression systems for use in prokaryotic host cells have been described, e.g., Terpe et al. (2006) *Appl Microbiol Biotechnol* 72:211-222. Commonly used expression systems for bacterial host cells (e.g., *E. coli*) include: the lac promoter, trc and tac promoter systems, T7 systems, phage promoter $P_L$, tetA promoter/operator, araBAD promoter, and rhaPBAD promoter systems. See, e.g., Polisky et al. (1976) *Proc Natl Acad Sci USA* 73:3900-3904; De Boer et al. (1983) *Proc Natl Acad Sci USA* 80:21-25; Brosius et al. (1985) *J Biol Chem* 260:3539-3541; Amann et al. (1983) *Gene* 25:167-178; and Quick and Wright (2002) *Proc Natl Acad Sci USA* 99:8597-8601. Another widely-used bacterial expression system is the pET vector expression system. Studier et al. (1986) *J Mol Biol* 189:113-130; Dietrich et al. (1991) *Eur J Biochem* 201:399-407; Lathrop et al. (1992) *Protein Expr Purif* 3:512-517; and Aukhil et al. (1993) *J Biol Chem* 268:2542-2553.

Several possible vector systems are available for the expression of recombinant polypeptides from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA* 78:2072) or Tn5 neo (Southern and Berg (1982) *Mol Appl Genet* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA,* 79:7147), cytomegalovirus, polyoma virus (Deans et al. (1984) *Proc Natl Acad Sci USA* 81:1292), or SV40 virus (Lusky and Botchan (1981) *Nature* 293:79).

The expression vectors can be introduced into cells in a manner suitable for subsequent expression of the nucleic acid. The method of introduction is largely dictated by the targeted cell type. Exemplary methods include $CaPO_4$ precipitation, liposome fusion, cationic liposomes, electroporation, viral infection, dextran-mediated transfection, polybrene-mediated transfection, protoplast fusion, and direct microinjection.

Appropriate host cells for the expression of recombinant proteins include yeast, bacteria, insect, plant, and mammalian cells. Of particular interest are bacteria such as *E. coli*, fungi such as *Saccharomyces cerevisiae* and *Pichia pastoris*, insect cells such as SF9, mammalian cell lines (e.g., human cell lines), as well as primary cell lines. In addition to *E. coli*, other commonly-used prokaryotic host cells include bacilli strains *B. megaterium, B. subtlis, B. brevis*, and *Caulobacter crescentus*.

A variant polypeptide or fragment thereof described herein can be expressed in mammalian cells or in other expression systems including but not limited to yeast, baculovirus, and even in vitro expression systems (see, e.g., Kaszubska et al. (2000) *Protein Expression and Purification* 18:213-220).

Following expression, the recombinant proteins can be isolated. The term "purified" or "isolated" as applied to any of the proteins described herein refers to a polypeptide that has been separated or purified from components (e.g., proteins or other naturally-occurring biological or organic molecules) which naturally accompany it, e.g., other proteins, lipids, and nucleic acid in a prokaryotic or eukaryotic cell expressing the proteins. Typically, a polypeptide is purified when it constitutes at least 60 (e.g., at least 65, 70, 75, 80, 85, 90, 92, 95, 97, or 99) %, by weight, of the total protein in a sample.

The recombinant proteins can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. Ultrafiltration and diafiltration techniques, in conjunction with protein concentration, are also useful. See, e.g., Scopes (1994) "*Protein Purification, 3rd edition*," Springer-Verlag, New York City, N.Y. The degree of purification necessary will vary depending on the desired use. In some instances, no purification of the expressed proteins will be necessary.

Methods for determining the yield or purity of a purified protein are known in the art and include, e.g., Bradford assay, UV spectroscopy, Biuret protein assay, Lowry protein assay, amido black protein assay, high performance liquid chromatography (HPLC), mass spectrometry (MS), and gel electrophoretic methods (e.g., using a protein stain such as Coomassie Blue or colloidal silver stain).

Exemplary methods for producing, expressing, and isolating a LDH from *E. coli* are exemplified in the working examples. Additional methods for producing a recombinant LDH (e.g., recombinant LDH from *B. sphaericus*) are described in, e.g., Li et al. (2009) *Appl Biochem Biotechnol* 158:343-351.

Applications

The variant polypeptides and enzymatically-active fragments thereof are useful in a number of applications. For example, the polypeptides and fragments can be used as control enzymes in screening methods designed to identify additional variant polypeptides and fragments capable of converting 2-oxonon-8-enoic acid, in the presence of an ammonia source, to LCAA, e.g., (S)-LCAA. Such methods would include, optionally, generating one or more (e.g., a library of) test variant leucine dehydrogenase polypeptides (e.g., substitution, insertion, or deletion variants of any one of SEQ ID NOs:1, 2, or 4-18). Methods for generating test variant polypeptides are described herein (supra) and exemplified in the working examples. The test variant polypeptides can be screened, e.g., using the LCAA production reaction described in Examples 1 and 2 below.

In addition, the variant polypeptides and enzymatically-active fragments thereof described herein are useful as enzyme catalysts for the conversion of 2-oxonon-8-enoic acid to (S)-LCAA. Such methods are described herein and exemplified in the working examples.

Kits

Also provided herein are kits containing one or more of the variant polypeptides or enzymatically-active fragments thereof and, optionally, instructions for carrying out a reaction to aminate an aliphatic keto acid. The variant polypeptides or fragments can be provided in solution, e.g., aqueous solution, or in lyophilized form. In the latter case, the kit can optionally include one or more buffers for reconstituting the lyophilized protein.

In some embodiments, the kits can include nicotinamide adenine dinucleotide (NAD), e.g., a reduced form of NAD and, optionally, appropriate reaction buffers. In some embodiments, the kits can include glucose. In some embodiments, the kits can further include a glucose dehydrogenase.

EXAMPLES

The following examples are intended to illustrate, not limit, the disclosure.

Example 1. Production of 2-aminonon-8-enoic Acid (LCAA) Using Leucine Dehydrogenase

*E. coli* cells were transformed with an expression vector encoding wild-type, *B. cereus* leucine dehydrogenase (LDH; having the amino acid sequence depicted in SEQ ID NO:1). LDH protein was expressed at 37° C. using standard molecular biology techniques. Briefly, seed cultures of 10 mL of LB media with 50 μg/mL ampicillin were inoculated with frozen cell stocks of *E. coli* containing the expression vector. The cultures were incubated at 37° C. and 250 rpm overnight. Expression cultures were inoculated with the seed culture at a 1:200 dilution and grown at 37° C. and 250 rotations per minute (rpm) until the culture reached an $OD_{600}$ of 0.5, at which time they were induced with 0.5 μL of 0.2 M IPTG. After induction, cultures were incubated at 37° C. for 18-24 hours.

Following expression, cultures were harvested by centrifugation (14,000 rpm for 3 min) and resuspended with 1/10th the original culture volume in B-PER™ Protein Extraction Reagent (Thermo Scientific, Rockford, Ill.). Alternatively, cell cultures could also be lysed by resuspension in buffer (i.e. 0.1 M phosphate buffer pH 7) followed by sonication. The resulting cell lysate was clarified by centrifugation at 14,000 rpm for 3 min. The supernatant was reserved as the cell-free extract LDH enzyme solution.

To produce (S)-LCAA from 2-oxonon-8-enoic acid, a reaction was performed under the following conditions. In 200 mL total volume and a buffered pH of 9.5, the aqueous reaction mixture contained 10 mM 2-oxonon-8-enoic acid, 12 mM glucose, 1 mM $NAD^+$, 50 mg of purified glucose dehydrogenase (GDH-105; Codexis, Redwood City, Calif.), 2 M $NH_4Cl/OH$, and approximately 60 mL/L of purified leucine dehydrogenase cell-free extract. FIG. 2 depicts the reaction scheme for converting 2-oxonon-8-enoic acid to (S)-LCAA using leucine dehydrogenase. The mixture was incubated at 30° C. and with shaking at 150 rpm for four hours.

Figure 3:
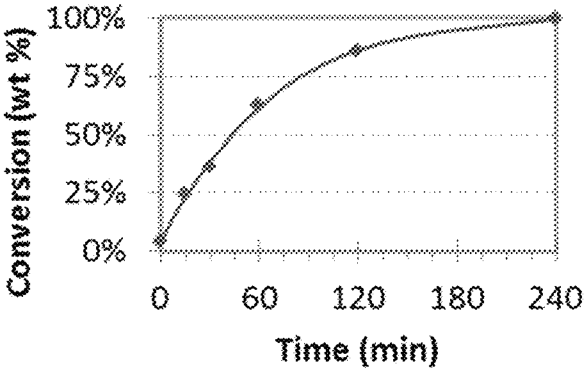
FIG. 3 is a line graph depicting the rate of conversion of 2-oxonon-8-enoic acid (substrate) to (S)-LCAA (product) using wild-type, full-length *Bacillus cereus* LDH. The Y-axis represents the percent conversion of substrate to product. The X-axis represents time in minutes.

Enzyme activity was measured spectrophotometrically by monitoring the consumption of NADH in the reductive amination at 340 nm. Activity was defined as the number of micromoles of NADH consumed in 1 minute (μmol $min^{-1}$). Aliquots of the reaction mixture were obtained periodically during the course of the reaction and subjected to analysis by high performance liquid chromatography (HPLC). As shown in FIG. 3, greater than 99.5% conversion of the substrate to LCAA was achieved by four hours.

Figure 4:
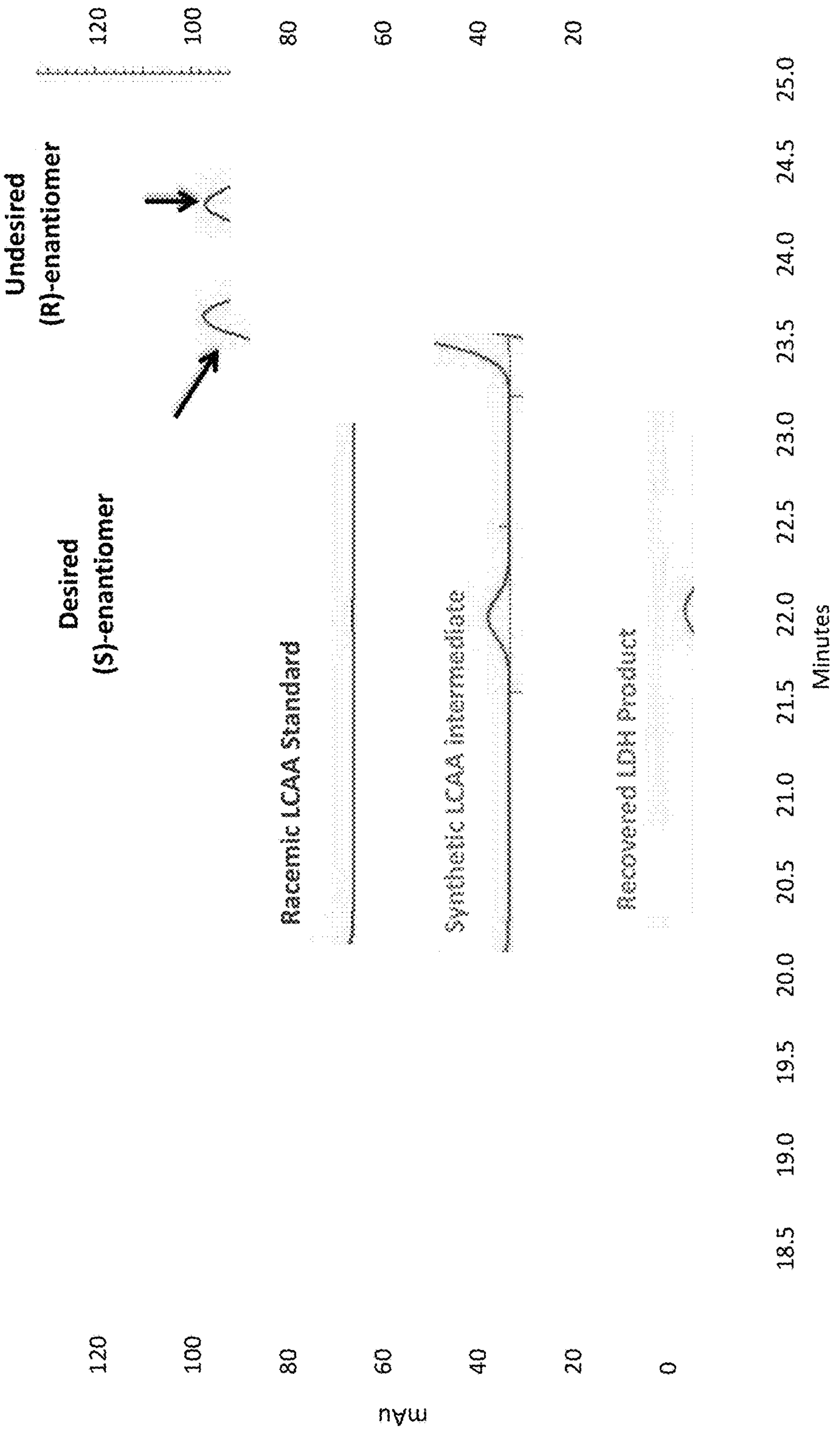
FIG. 4 is a chromatograph depicting the percentage of (S)-enantiomer of LCAA produced by the LDH-driven enzymatic reaction. Analyses of a racemic standard having both (S) and (R) forms, as well as chemically synthesized (S)-LCAA, were also performed (and shown) for reference.

To determine what percentage of the LCAA reaction product of the reaction was (S)-LCAA, aliquots of the reaction mixture were analyzed using high performance liquid chromatography (HPLC). As shown in FIG. 4, greater than 99.5% of the reaction product was the desired (S)-enantiomer.

Example 2. Exemplary Variant *B. cereus* LDH Polypeptides

Figure 5:
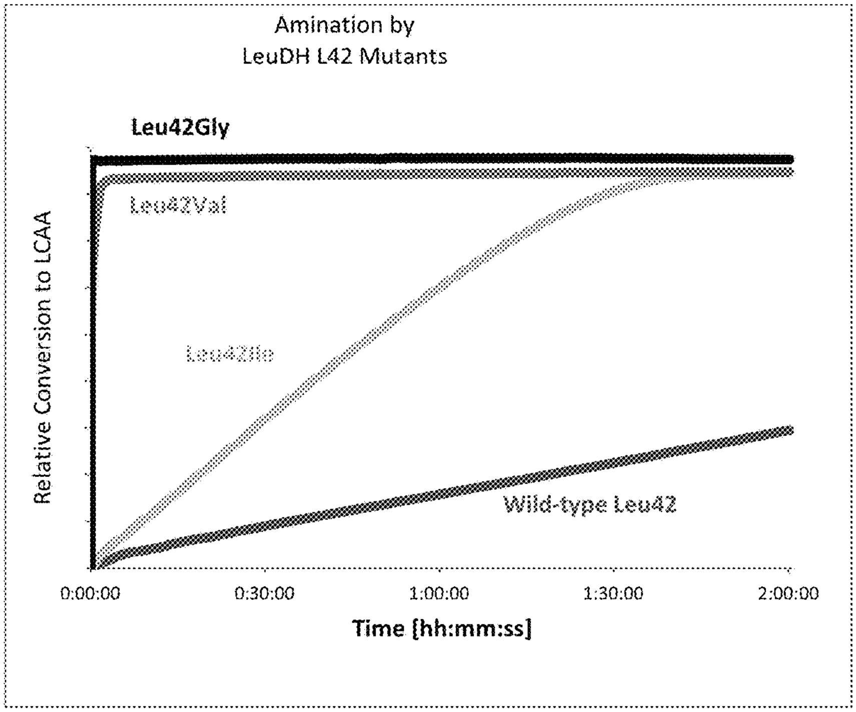
FIG. 5 is a line graph depicting the relative reaction rates of wild-type LDH and L32I, L42V, and L42G LDH variants for converting 2-oxonon-8-enoic acid (substrate) to (S)-LCAA. The Y-axis represents the relative percent conversion of substrate to product. The X-axis represents time.

To increase the affinity of LDH for the 2-oxonon-8-enoic acid substrate and, thus, enhance the enzyme's activity for producing (S)-LCAA, amino acid substitutions were made within the region of LDH that binds to the substrate. Specifically, amino acid substitutions were introduced at position 42 of *B. cereus* leucine dehydrogenase (SEQ ID NO:1) using standard mutagenesis techniques. Wild-type *B. cereus* LDH, along with 19 variants (one for each amino acid substitution at position 42) were expressed and isolated as described in Example 1. The enzymatic activity of the variant proteins was evaluated alongside wild-type *B. cereus* LDH in the reaction described in Example 1. As shown in FIG. 5, three of the substitution variants (L42I, L42V, and L42G) exhibited significantly enhanced activity (a greater reaction rate), relative to wild-type *B. cereus* LDH. L42G and L42V exhibited an approximately $1\times10^3$ increase in reaction rate, relative to wild-type *B. cereus* LDH. The L42A, L42T, and L42S variants also exhibited enhanced activity relative to wild-type *B. cereus* LDH. The L42A variant had a similar level of enzymatic activity to the L42V variant LDH enzyme. By contrast, L42D, L42K, L42Y, and L42H variants possessed reduced activity, relative to wild-type *B. cereus* LDH, under these reaction conditions. While the disclosure is not bound by any particular theory or mechanism of action, the substitutions that increased the enzymatic activity of the LDH enzyme are believed to have increased the depth of the substrate binding pocket in LDH and thereby increased the affinity of LDH for the 2-oxonon-8-enoic acid substrate.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What we claim is:

1. A polypeptide, comprising:

(a) the amino acid sequence of any one of SEQ ID NOS:2 and 13-18, wherein X is not leucine;

(b) an amino acid sequence that is at least 95% identical to: (i) amino acids 6 to 238 of SEQ ID NO:2; (ii) amino acids 7 to 237 of SEQ ID NO:13; (iii) amino acids 4 to 236 of SEQ ID NO:14; (iv) amino acids 4 to 236 of SEQ ID NO:15; (v) amino acids 4 to 236 of SEQ ID NO:16; (vi) amino acids 4 to 236 of SEQ ID NO:17; or (vii) amino acids 4 to 236 of SEQ ID NO:18, wherein X is not leucine;

(c) an amino acid sequence that is at least 95% identical to: (i) amino acids 6 to 298 of SEQ ID NO:2; (ii) amino acids 7 to 297 of SEQ ID NO:13; (iii) amino acids 4 to 296 of SEQ ID NO:14; (iv) amino acids 4 to 296 of SEQ ID NO:15; (v) amino acids 4 to 296 of SEQ ID NO:16; (vi) amino acids 4 to 296 of SEQ ID NO:17; or (vii) amino acids 4 to 296 of SEQ ID NO:18, wherein X is not leucine; or (d) the amino acid sequence of SEQ ID NO: 4, 5, 6, or 20;

wherein the polypeptide is isolated and wherein the polypeptide has the ability to convert 2-oxonon-8-enoic acid, in the presence of an ammonia source, to 2-aminonon-8-enoic acid; and X is isoleucine, valine, glycine, alanine, serine, or threonine.

2. The polypeptide of claim 1, wherein X is isoleucine.

3. The polypeptide of claim 1, wherein X is valine.

4. The polypeptide of claim 1, wherein X is glycine.

5. The polypeptide of claim 1, wherein X is alanine.

6. The polypeptide of claim 1, wherein X is serine or threonine.

7. The polypeptide of claim 1, wherein the polypeptide comprises the amino acid sequence of any one of SEQ ID NOS:2 and 13-18.

8. The polypeptide of claim 1, wherein the polypeptide comprises an amino acid sequence that is at least 95% identical to: (i) amino acids 6 to 238 of SEQ ID NO:2; (ii) amino acids 7 to 237 of SEQ ID NO:13; (iii) amino acids 4 to 236 of SEQ ID NO:14; (iv) amino acids 4 to 236 of SEQ ID NO:15; (v) amino acids 4 to 236 of SEQ ID NO:16; (vi) amino acids 4 to 236 of SEQ ID NO:17; or (vii) amino acids 4 to 236 of SEQ ID NO:18.

9. The polypeptide of claim 1, wherein the polypeptide comprises an amino acid sequence that is at least 95% identical to: (i) amino acids 6 to 298 of SEQ ID NO:2; (ii) amino acids 7 to 297 of SEQ ID NO:13; (iii) amino acids 4 to 296 of SEQ ID NO:14; (iv) amino acids 4 to 296 of SEQ ID NO:15; (v) amino acids 4 to 296 of SEQ ID NO:16; (vi) amino acids 4 to 296 of SEQ ID NO:17; or (vii) amino acids 4 to 296 of SEQ ID NO:18.

10. The polypeptide of claim 1, wherein the polypeptide comprises the amino acid sequence of SEQ ID NO: 4, 5, 6, or 20.

11. The polypeptide of claim 1, wherein the polypeptide comprises an amino acid sequence that is at least 95% identical to amino acids 6 to 238 of SEQ ID NO:2.

12. The polypeptide of claim 11, wherein X is alanine.

13. The polypeptide of claim 7, wherein the amino acid sequence is SEQ ID NO:2.

14. The polypeptide of claim 13, wherein X is alanine.

* * * * *

SEQUENCE LISTING

```
<160> NUMBER OF SEQ ID NOS: 20

<210> SEQ ID NO 1
<211> LENGTH: 366
<212> TYPE: PRT
<213> ORGANISM: Bacillus cereus

<400> SEQUENCE: 1

Met Thr Leu Glu Ile Phe Glu Tyr Leu Glu Lys Tyr Asp Tyr Glu Gln
1               5                   10                  15

Val Val Phe Cys Gln Asp Lys Glu Ser Gly Leu Lys Ala Ile Ile Ala
            20                  25                  30

Ile His Asp Thr Thr Leu Gly Pro Ala Leu Gly Gly Thr Arg Met Trp
        35                  40                  45

Thr Tyr Asp Ser Glu Glu Ala Ala Ile Glu Asp Ala Leu Arg Leu Ala
    50                  55                  60

Lys Gly Met Thr Tyr Lys Asn Ala Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160

Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
    210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
            260                 265                 270

Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
```

```
    290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335

Ala Asp Arg Leu Ala Glu Glu Arg Ile Ala Ser Leu Lys Asn Ser Arg
            340                 345                 350

Ser Thr Tyr Leu Arg Asn Gly His Asp Ile Ile Ser Arg Arg
        355                 360                 365


<210> SEQ ID NO 2
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: Any amino acid except Leu

<400> SEQUENCE: 2

Met Thr Leu Glu Ile Phe Glu Tyr Leu Glu Lys Tyr Asp Tyr Glu Gln
1               5                   10                  15

Val Val Phe Cys Gln Asp Lys Glu Ser Gly Leu Lys Ala Ile Ile Ala
            20                  25                  30

Ile His Asp Thr Thr Leu Gly Pro Ala Xaa Gly Gly Thr Arg Met Trp
        35                  40                  45

Thr Tyr Asp Ser Glu Glu Ala Ala Ile Glu Asp Ala Leu Arg Leu Ala
    50                  55                  60

Lys Gly Met Thr Tyr Lys Asn Ala Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160

Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
    210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
            260                 265                 270
```

```
Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
    290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335

Ala Asp Arg Leu Ala Glu Glu Arg Ile Ala Ser Leu Lys Asn Ser Arg
            340                 345                 350

Ser Thr Tyr Leu Arg Asn Gly His Asp Ile Ile Ser Arg Arg
        355                 360                 365


<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid except Leu

<400> SEQUENCE: 3

Gly Pro Ala Xaa Gly Gly
1               5


<210> SEQ ID NO 4
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Thr Leu Glu Ile Phe Glu Tyr Leu Glu Lys Tyr Asp Tyr Glu Gln
1               5                   10                  15

Val Val Phe Cys Gln Asp Lys Glu Ser Gly Leu Lys Ala Ile Ile Ala
            20                  25                  30

Ile His Asp Thr Thr Leu Gly Pro Ala Ile Gly Gly Thr Arg Met Trp
        35                  40                  45

Thr Tyr Asp Ser Glu Glu Ala Ala Ile Glu Asp Ala Leu Arg Leu Ala
    50                  55                  60

Lys Gly Met Thr Tyr Lys Asn Ala Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160

Lys Ala Ala Ala Lys Glu Ala Phe Gly Thr Asp Asn Leu Glu Gly Lys
```

```
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
    210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
            260                 265                 270

Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
    290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335

Ala Asp Arg Leu Ala Glu Glu Arg Ile Ala Ser Leu Lys Asn Ser Arg
            340                 345                 350

Ser Thr Tyr Leu Arg Asn Gly His Asp Ile Ile Ser Arg Arg
        355                 360                 365


<210> SEQ ID NO 5
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Thr Leu Glu Ile Phe Glu Tyr Leu Glu Lys Tyr Asp Tyr Glu Gln
1               5                   10                  15

Val Val Phe Cys Gln Asp Lys Glu Ser Gly Leu Lys Ala Ile Ile Ala
            20                  25                  30

Ile His Asp Thr Thr Leu Gly Pro Ala Val Gly Gly Thr Arg Met Trp
        35                  40                  45

Thr Tyr Asp Ser Glu Glu Ala Ala Ile Glu Asp Ala Leu Arg Leu Ala
    50                  55                  60

Lys Gly Met Thr Tyr Lys Asn Ala Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160
```

-continued

```
Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
    210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
            260                 265                 270

Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
    290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335

Ala Asp Arg Leu Ala Glu Glu Arg Ile Ala Ser Leu Lys Asn Ser Arg
            340                 345                 350

Ser Thr Tyr Leu Arg Asn Gly His Asp Ile Ile Ser Arg Arg
        355                 360                 365


<210> SEQ ID NO 6
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Thr Leu Glu Ile Phe Glu Tyr Leu Glu Lys Tyr Asp Tyr Glu Gln
1               5                   10                  15

Val Val Phe Cys Gln Asp Lys Glu Ser Gly Leu Lys Ala Ile Ile Ala
            20                  25                  30

Ile His Asp Thr Thr Leu Gly Pro Ala Gly Gly Gly Thr Arg Met Trp
        35                  40                  45

Thr Tyr Asp Ser Glu Glu Ala Ala Ile Glu Asp Ala Leu Arg Leu Ala
    50                  55                  60

Lys Gly Met Thr Tyr Lys Asn Ala Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160
```

```
Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
    210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
            260                 265                 270

Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
    290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335

Ala Asp Arg Leu Ala Glu Glu Arg Ile Ala Ser Leu Lys Asn Ser Arg
            340                 345                 350

Ser Thr Tyr Leu Arg Asn Gly His Asp Ile Ile Ser Arg Arg
        355                 360                 365


<210> SEQ ID NO 7
<211> LENGTH: 351
<212> TYPE: PRT
<213> ORGANISM: Chlamydia pneumoniae

<400> SEQUENCE: 7

Met Lys Tyr Ser Leu Asn Phe Lys Glu Ile Lys Ile Asp Asp Tyr Glu
1               5                   10                  15

Arg Val Ile Glu Val Thr Cys Ser Lys Val Arg Leu His Ala Ile Ile
            20                  25                  30

Ala Ile His Gln Thr Ala Val Gly Pro Ala Leu Gly Gly Val Arg Ala
        35                  40                  45

Ser Leu Tyr Ser Ser Phe Glu Asp Ala Cys Thr Asp Ala Leu Arg Leu
    50                  55                  60

Ala Arg Gly Met Thr Tyr Lys Ala Ile Ile Ser Asn Thr Gly Thr Gly
65                  70                  75                  80

Gly Gly Lys Ser Val Ile Ile Leu Pro Gln Asp Ala Pro Ser Leu Thr
                85                  90                  95

Glu Asp Met Leu Arg Ala Phe Gly Gln Ala Val Asn Ala Leu Glu Gly
            100                 105                 110

Thr Tyr Ile Cys Ala Glu Asp Leu Gly Val Ser Ile Asn Asp Ile Ser
        115                 120                 125

Ile Val Ala Glu Glu Thr Pro Tyr Val Cys Gly Ile Ala Asp Val Ser
    130                 135                 140

Gly Asp Pro Ser Ile Tyr Thr Ala His Gly Gly Phe Leu Cys Ile Lys
145                 150                 155                 160

Glu Thr Ala Lys Tyr Leu Trp Gly Ser Ser Ser Leu Arg Gly Lys Lys
```

-continued

```
                165                 170                 175

Ile Ala Ile Gln Gly Ile Gly Ser Val Gly Arg Arg Leu Leu Gln Ser
            180                 185                 190

Leu Phe Phe Glu Gly Ala Glu Leu Tyr Val Ala Asp Val Leu Glu Arg
        195                 200                 205

Ala Val Gln Asp Ala Ala Arg Leu Tyr Gly Ala Thr Ile Val Pro Thr
    210                 215                 220

Glu Glu Ile His Ala Leu Glu Cys Asp Ile Phe Ser Pro Cys Ala Arg
225                 230                 235                 240

Gly Asn Val Ile Arg Lys Asp Asn Leu Ala Asp Leu Asn Cys Lys Ala
                245                 250                 255

Ile Val Gly Val Ala Asn Asn Gln Leu Glu Asp Ser Ser Ala Gly Met
            260                 265                 270

Met Leu His Glu Arg Gly Ile Leu Tyr Gly Pro Asp Tyr Leu Val Asn
        275                 280                 285

Ala Gly Gly Leu Leu Asn Val Ala Ala Ala Ile Glu Gly Arg Val Tyr
    290                 295                 300

Ala Pro Lys Glu Val Leu Leu Lys Val Glu Glu Leu Pro Ile Val Leu
305                 310                 315                 320

Ser Lys Leu Tyr Asn Gln Ser Lys Thr Thr Gly Lys Asp Leu Val Ala
                325                 330                 335

Leu Ser Asp Ser Phe Val Glu Asp Lys Leu Leu Ala Tyr Thr Ser
            340                 345                 350


<210> SEQ ID NO 8
<211> LENGTH: 366
<212> TYPE: PRT
<213> ORGANISM: Thermoactinomyces intermedius

<400> SEQUENCE: 8

Met Lys Ile Phe Asp Tyr Met Glu Lys Tyr Asp Tyr Glu Gln Leu Val
1               5                   10                  15

Met Cys Gln Asp Lys Glu Ser Gly Leu Lys Ala Ile Ile Cys Ile His
            20                  25                  30

Val Thr Thr Leu Gly Pro Ala Leu Gly Gly Met Arg Met Trp Thr Tyr
        35                  40                  45

Ala Ser Glu Glu Glu Ala Ile Glu Asp Ala Leu Arg Leu Gly Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Ala Met Phe
                85                  90                  95

Arg Ala Leu Gly Arg Phe Ile Gln Gly Leu Asn Gly Arg Tyr Ile Thr
            100                 105                 110

Ala Glu Asp Val Gly Thr Thr Val Glu Asp Met Asp Ile Ile His Glu
        115                 120                 125

Glu Thr Arg Tyr Val Thr Gly Val Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Glu Ala Phe Gly Asp Asp Ser Leu Glu Gly Lys Val Val
                165                 170                 175

Ala Val Gln Gly Val Gly His Val Ala Tyr Glu Leu Cys Lys His Leu
            180                 185                 190
```

```
His Asn Glu Gly Ala Lys Leu Ile Val Thr Asp Ile Asn Lys Glu Asn
        195                 200                 205

Ala Asp Arg Ala Val Gln Glu Phe Gly Ala Glu Phe Val His Pro Asp
    210                 215                 220

Lys Ile Tyr Asp Val Glu Cys Asp Ile Phe Ala Pro Cys Ala Leu Gly
225                 230                 235                 240

Ala Ile Ile Asn Asp Glu Thr Ile Glu Arg Leu Lys Cys Lys Val Val
                245                 250                 255

Ala Gly Ser Ala Asn Asn Gln Leu Lys Glu Glu Arg His Gly Lys Met
            260                 265                 270

Leu Glu Glu Lys Gly Ile Val Tyr Ala Pro Asp Tyr Val Ile Asn Ala
        275                 280                 285

Gly Gly Val Ile Asn Val Ala Asp Glu Leu Leu Gly Tyr Asn Arg Glu
    290                 295                 300

Arg Ala Met Lys Lys Val Glu Gly Ile Tyr Asp Lys Ile Leu Lys Val
305                 310                 315                 320

Phe Glu Ile Ala Lys Arg Asp Gly Ile Pro Ser Tyr Leu Ala Ala Asp
                325                 330                 335

Arg Met Ala Glu Glu Arg Ile Glu Met Met Arg Lys Thr Arg Ser Thr
            340                 345                 350

Phe Leu Gln Asp Gln Arg Asn Leu Ile Asn Phe Asn Asn Lys
        355                 360                 365
```

```
<210> SEQ ID NO 9
<211> LENGTH: 364
<212> TYPE: PRT
<213> ORGANISM: Bacillus subtilis

<400> SEQUENCE: 9

Met Glu Leu Phe Lys Tyr Met Glu Lys Tyr Asp Tyr Glu Gln Leu Val
1               5                   10                  15

Phe Cys Gln Asp Glu Gln Ser Gly Leu Lys Ala Ile Ile Ala Ile His
            20                  25                  30

Asp Thr Thr Leu Gly Pro Ala Leu Gly Gly Thr Arg Met Trp Thr Tyr
        35                  40                  45

Glu Asn Glu Glu Ala Ala Ile Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Glu Met Phe
                85                  90                  95

Arg Ala Phe Gly Arg Tyr Ile Gln Gly Leu Asn Gly Arg Tyr Ile Thr
            100                 105                 110

Ala Glu Asp Val Gly Thr Thr Val Glu Asp Met Asp Ile Ile His Asp
        115                 120                 125

Glu Thr Asp Tyr Val Thr Gly Ile Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Ala Ala Phe Gly Thr Asp Ser Leu Glu Gly Lys Thr Ile
                165                 170                 175

Ala Val Gln Gly Val Gly Asn Val Ala Tyr Asn Leu Cys Arg His Leu
            180                 185                 190

His Glu Glu Gly Ala Asn Leu Ile Val Thr Asp Ile Asn Lys Gln Ser
        195                 200                 205
```

```
Val Gln Arg Ala Val Glu Asp Phe Gly Ala Arg Ala Val Asp Pro Asp
    210                 215                 220

Asp Ile Tyr Ser Gln Asp Cys Asp Ile Tyr Ala Pro Cys Ala Leu Gly
225                 230                 235                 240

Ala Thr Ile Asn Asp Asp Thr Ile Lys Gln Leu Lys Ala Lys Val Ile
                245                 250                 255

Ala Gly Ala Ala Asn Asn Gln Leu Lys Glu Thr Arg His Gly Asp Gln
            260                 265                 270

Ile His Glu Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Ala Glu
    290                 295                 300

Arg Ala Leu Lys Lys Val Glu Gly Ile Tyr Gly Asn Ile Glu Arg Val
305                 310                 315                 320

Leu Glu Ile Ser Gln Arg Asp Gly Ile Pro Ala Tyr Leu Ala Ala Asp
                325                 330                 335

Arg Leu Ala Glu Glu Arg Ile Glu Arg Met Arg Arg Ser Arg Ser Gln
            340                 345                 350

Phe Leu Gln Asn Gly His Ser Val Leu Ser Arg Arg
        355                 360


<210> SEQ ID NO 10
<211> LENGTH: 364
<212> TYPE: PRT
<213> ORGANISM: Bacillus licheniformis

<400> SEQUENCE: 10

Met Glu Leu Phe Arg Tyr Met Glu Gln Tyr Asp Tyr Glu Gln Leu Val
1               5                   10                  15

Phe Cys Gln Asp Lys Gln Ser Gly Leu Lys Ala Ile Ile Ala Ile His
            20                  25                  30

Asp Thr Thr Leu Gly Pro Ala Leu Gly Gly Thr Arg Met Trp Thr Tyr
        35                  40                  45

Glu Ser Glu Glu Ala Ala Ile Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Glu Met Phe
                85                  90                  95

Arg Ala Phe Gly Arg Tyr Ile Gln Gly Leu Asn Gly Arg Tyr Ile Thr
            100                 105                 110

Ala Glu Asp Val Gly Thr Thr Val Glu Asp Met Asp Ile Ile His Asp
        115                 120                 125

Glu Thr Asp Phe Val Thr Gly Ile Ser Pro Ala Phe Gly Ser Ser Gly
    130                 135                 140

Asn Pro Ser Pro Val Thr Ala Tyr Gly Val Tyr Lys Gly Met Lys Ala
145                 150                 155                 160

Ala Ala Lys Ala Ala Phe Gly Thr Asp Ser Leu Glu Gly Lys Thr Val
                165                 170                 175

Ala Val Gln Gly Val Gly Asn Val Ala Tyr Asn Leu Cys Arg His Leu
            180                 185                 190

His Glu Glu Gly Ala Lys Leu Ile Val Thr Asp Ile Asn Lys Glu Ala
        195                 200                 205

Val Glu Arg Ala Val Ala Glu Phe Gly Ala Arg Ala Val Asp Pro Asp
```

```
    210                 215                 220

Asp Ile Tyr Ser Gln Glu Cys Asp Ile Tyr Ala Pro Cys Ala Leu Gly
225                 230                 235                 240

Ala Thr Ile Asn Asp Asp Thr Ile Pro Gln Leu Lys Ala Lys Val Ile
                245                 250                 255

Ala Gly Ala Ala Asn Asn Gln Leu Lys Glu Thr Arg His Gly Asp Gln
            260                 265                 270

Ile His Asp Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Ser Glu
    290                 295                 300

Arg Ala Leu Lys Lys Val Glu Gly Ile Tyr Gly Asn Ile Glu Arg Val
305                 310                 315                 320

Leu Glu Ile Ser Lys Arg Asp Arg Ile Pro Thr Tyr Leu Ala Ala Asp
                325                 330                 335

Arg Leu Ala Glu Glu Arg Ile Glu Arg Met Arg Gln Ser Arg Ser Gln
            340                 345                 350

Phe Leu Gln Asn Gly His His Ile Leu Ser Arg Arg
        355                 360


<210> SEQ ID NO 11
<211> LENGTH: 367
<212> TYPE: PRT
<213> ORGANISM: Geobacillus stearothermophilus

<400> SEQUENCE: 11

Met Glu Leu Phe Lys Tyr Met Glu Thr Tyr Asp Tyr Glu Gln Val Leu
1               5                   10                  15

Phe Cys Gln Asp Lys Glu Ser Gly Leu Lys Ala Ile Ile Ala Ile His
            20                  25                  30

Asp Thr Thr Leu Gly Pro Ala Leu Gly Gly Thr Arg Met Trp Met Tyr
        35                  40                  45

Asn Ser Glu Glu Glu Ala Leu Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Ala Met Phe
                85                  90                  95

Arg Ala Phe Gly Arg Phe Ile Gln Gly Leu Asn Gly Arg Tyr Ile Thr
            100                 105                 110

Ala Glu Asp Val Gly Thr Thr Val Ala Asp Met Asp Ile Ile Tyr Gln
        115                 120                 125

Glu Thr Asp Tyr Val Thr Gly Ile Ser Pro Glu Phe Gly Ser Ser Gly
    130                 135                 140

Asn Pro Ser Pro Ala Thr Ala Tyr Gly Val Tyr Arg Gly Met Lys Ala
145                 150                 155                 160

Ala Ala Lys Glu Ala Phe Gly Ser Asp Ser Leu Glu Gly Lys Val Val
                165                 170                 175

Ala Val Gln Gly Val Gly Asn Val Ala Tyr His Leu Cys Arg His Leu
            180                 185                 190

His Glu Glu Gly Ala Lys Leu Ile Val Thr Asp Ile Asn Lys Glu Val
        195                 200                 205

Val Ala Arg Ala Val Glu Glu Phe Gly Ala Lys Ala Val Asp Pro Asn
    210                 215                 220
```

-continued

```
Asp Ile Tyr Gly Val Glu Cys Asp Ile Phe Ala Pro Cys Ala Leu Gly
225                 230                 235                 240

Gly Ile Ile Asn Asp Gln Thr Ile Pro Gln Leu Lys Ala Lys Val Ile
                245                 250                 255

Ala Gly Ser Ala Asp Asn Gln Leu Lys Glu Pro Arg His Gly Asp Ile
            260                 265                 270

Ile His Glu Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Arg Glu
    290                 295                 300

Arg Ala Met Lys Lys Ile Glu Gln Ile Tyr Asp Asn Ile Glu Lys Val
305                 310                 315                 320

Phe Ala Ile Ala Lys Arg Asp Asn Ile Pro Thr Tyr Val Ala Ala Asp
                325                 330                 335

Arg Met Ala Glu Glu Arg Ile Glu Thr Met Arg Lys Ala Arg Ser Pro
            340                 345                 350

Phe Leu Gln Asn Gly His His Ile Leu Ser Arg Arg Arg Ala Arg
        355                 360                 365


<210> SEQ ID NO 12
<211> LENGTH: 364
<212> TYPE: PRT
<213> ORGANISM: Lysinibacillus sphaericus

<400> SEQUENCE: 12

Met Glu Ile Phe Lys Tyr Met Glu Lys Tyr Asp Tyr Glu Gln Leu Val
1               5                   10                  15

Phe Cys Gln Asp Glu Ala Ser Gly Leu Lys Ala Ile Ile Ala Ile His
            20                  25                  30

Asp Thr Thr Leu Gly Pro Ala Leu Gly Gly Ala Arg Met Trp Thr Tyr
        35                  40                  45

Ala Thr Glu Glu Asn Ala Ile Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Phe Lys Asp Lys Asn Glu Glu Met Phe
                85                  90                  95

Arg Ala Leu Gly Arg Phe Ile Gln Gly Leu Asn Gly Arg Tyr Ile Thr
            100                 105                 110

Ala Glu Asp Val Gly Thr Thr Val Thr Asp Met Asp Leu Ile His Glu
        115                 120                 125

Glu Thr Asn Tyr Val Thr Gly Ile Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Glu Ala Phe Gly Thr Asp Met Leu Glu Gly Arg Thr Ile
                165                 170                 175

Ser Val Gln Gly Leu Gly Asn Val Ala Tyr Lys Leu Cys Glu Tyr Leu
            180                 185                 190

His Asn Glu Gly Ala Lys Leu Val Val Thr Asp Ile Asn Gln Ala Ala
        195                 200                 205

Ile Asp Arg Val Val Asn Asp Phe Gly Ala Thr Ala Val Ala Pro Asp
    210                 215                 220

Glu Ile Tyr Ser Gln Glu Val Asp Ile Phe Ser Pro Cys Ala Leu Gly
225                 230                 235                 240
```

```
Ala Ile Leu Asn Asp Glu Thr Ile Pro Gln Leu Lys Ala Lys Val Ile
                245                 250                 255

Ala Gly Ser Ala Asn Asn Gln Leu Gln Asp Ser Arg His Gly Asp Tyr
            260                 265                 270

Leu His Glu Leu Gly Ile Val Tyr Ala Pro Asp Tyr Val Ile Asn Ala
        275                 280                 285

Gly Gly Val Ile Asn Val Ala Asp Glu Leu Tyr Gly Tyr Asn Arg Glu
    290                 295                 300

Arg Ala Leu Lys Arg Val Asp Gly Ile Tyr Asp Ser Ile Glu Lys Ile
305                 310                 315                 320

Phe Glu Ile Ser Lys Arg Asp Ser Ile Pro Thr Tyr Val Ala Ala Asn
                325                 330                 335

Arg Leu Ala Glu Glu Arg Ile Ala Arg Val Ala Lys Ser Arg Ser Gln
            340                 345                 350

Phe Leu Lys Asn Glu Lys Asn Ile Leu Asn Gly Arg
        355                 360


<210> SEQ ID NO 13
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Any amino acid except Leu

<400> SEQUENCE: 13

Met Lys Tyr Ser Leu Asn Phe Lys Glu Ile Lys Ile Asp Asp Tyr Glu
1               5                   10                  15

Arg Val Ile Glu Val Thr Cys Ser Lys Val Arg Leu His Ala Ile Ile
            20                  25                  30

Ala Ile His Gln Thr Ala Val Gly Pro Ala Xaa Gly Gly Val Arg Ala
        35                  40                  45

Ser Leu Tyr Ser Ser Phe Glu Asp Ala Cys Thr Asp Ala Leu Arg Leu
    50                  55                  60

Ala Arg Gly Met Thr Tyr Lys Ala Ile Ile Ser Asn Thr Gly Thr Gly
65                  70                  75                  80

Gly Gly Lys Ser Val Ile Ile Leu Pro Gln Asp Ala Pro Ser Leu Thr
                85                  90                  95

Glu Asp Met Leu Arg Ala Phe Gly Gln Ala Val Asn Ala Leu Glu Gly
            100                 105                 110

Thr Tyr Ile Cys Ala Glu Asp Leu Gly Val Ser Ile Asn Asp Ile Ser
        115                 120                 125

Ile Val Ala Glu Glu Thr Pro Tyr Val Cys Gly Ile Ala Asp Val Ser
    130                 135                 140

Gly Asp Pro Ser Ile Tyr Thr Ala His Gly Gly Phe Leu Cys Ile Lys
145                 150                 155                 160

Glu Thr Ala Lys Tyr Leu Trp Gly Ser Ser Ser Leu Arg Gly Lys Lys
                165                 170                 175

Ile Ala Ile Gln Gly Ile Gly Ser Val Gly Arg Arg Leu Leu Gln Ser
            180                 185                 190

Leu Phe Phe Glu Gly Ala Glu Leu Tyr Val Ala Asp Val Leu Glu Arg
        195                 200                 205
```

```
Ala Val Gln Asp Ala Ala Arg Leu Tyr Gly Ala Thr Ile Val Pro Thr
    210                 215                 220

Glu Glu Ile His Ala Leu Glu Cys Asp Ile Phe Ser Pro Cys Ala Arg
225                 230                 235                 240

Gly Asn Val Ile Arg Lys Asp Asn Leu Ala Asp Leu Asn Cys Lys Ala
                245                 250                 255

Ile Val Gly Val Ala Asn Asn Gln Leu Glu Asp Ser Ser Ala Gly Met
            260                 265                 270

Met Leu His Glu Arg Gly Ile Leu Tyr Gly Pro Asp Tyr Leu Val Asn
        275                 280                 285

Ala Gly Gly Leu Leu Asn Val Ala Ala Ala Ile Glu Gly Arg Val Tyr
    290                 295                 300

Ala Pro Lys Glu Val Leu Leu Lys Val Glu Glu Leu Pro Ile Val Leu
305                 310                 315                 320

Ser Lys Leu Tyr Asn Gln Ser Lys Thr Thr Gly Lys Asp Leu Val Ala
                325                 330                 335

Leu Ser Asp Ser Phe Val Glu Asp Lys Leu Leu Ala Tyr Thr Ser
            340                 345                 350


<210> SEQ ID NO 14
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Any amino acid except Leu

<400> SEQUENCE: 14

Met Lys Ile Phe Asp Tyr Met Glu Lys Tyr Asp Tyr Glu Gln Leu Val
1               5                   10                  15

Met Cys Gln Asp Lys Glu Ser Gly Leu Lys Ala Ile Ile Cys Ile His
            20                  25                  30

Val Thr Thr Leu Gly Pro Ala Xaa Gly Gly Met Arg Met Trp Thr Tyr
        35                  40                  45

Ala Ser Glu Glu Glu Ala Ile Glu Asp Ala Leu Arg Leu Gly Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Ala Met Phe
                85                  90                  95

Arg Ala Leu Gly Arg Phe Ile Gln Gly Leu Asn Gly Arg Tyr Ile Thr
            100                 105                 110

Ala Glu Asp Val Gly Thr Thr Val Glu Asp Met Asp Ile Ile His Glu
        115                 120                 125

Glu Thr Arg Tyr Val Thr Gly Val Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Glu Ala Phe Gly Asp Asp Ser Leu Glu Gly Lys Val Val
                165                 170                 175

Ala Val Gln Gly Val Gly His Val Ala Tyr Glu Leu Cys Lys His Leu
            180                 185                 190

His Asn Glu Gly Ala Lys Leu Ile Val Thr Asp Ile Asn Lys Glu Asn
```

-continued

```
        195                 200                 205

Ala Asp Arg Ala Val Gln Glu Phe Gly Ala Glu Phe Val His Pro Asp
    210                 215                 220

Lys Ile Tyr Asp Val Glu Cys Asp Ile Phe Ala Pro Cys Ala Leu Gly
225                 230                 235                 240

Ala Ile Ile Asn Asp Glu Thr Ile Glu Arg Leu Lys Cys Lys Val Val
                245                 250                 255

Ala Gly Ser Ala Asn Asn Gln Leu Lys Glu Glu Arg His Gly Lys Met
            260                 265                 270

Leu Glu Glu Lys Gly Ile Val Tyr Ala Pro Asp Tyr Val Ile Asn Ala
        275                 280                 285

Gly Gly Val Ile Asn Val Ala Asp Glu Leu Leu Gly Tyr Asn Arg Glu
    290                 295                 300

Arg Ala Met Lys Lys Val Glu Gly Ile Tyr Asp Lys Ile Leu Lys Val
305                 310                 315                 320

Phe Glu Ile Ala Lys Arg Asp Gly Ile Pro Ser Tyr Leu Ala Ala Asp
                325                 330                 335

Arg Met Ala Glu Glu Arg Ile Glu Met Met Arg Lys Thr Arg Ser Thr
            340                 345                 350

Phe Leu Gln Asp Gln Arg Asn Leu Ile Asn Phe Asn Asn Lys
        355                 360                 365


<210> SEQ ID NO 15
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Any amino acid except Leu

<400> SEQUENCE: 15

Met Glu Leu Phe Lys Tyr Met Glu Lys Tyr Asp Tyr Glu Gln Leu Val
1               5                   10                  15

Phe Cys Gln Asp Glu Gln Ser Gly Leu Lys Ala Ile Ile Ala Ile His
            20                  25                  30

Asp Thr Thr Leu Gly Pro Ala Xaa Gly Gly Thr Arg Met Trp Thr Tyr
        35                  40                  45

Glu Asn Glu Glu Ala Ala Ile Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Glu Met Phe
                85                  90                  95

Arg Ala Phe Gly Arg Tyr Ile Gln Gly Leu Asn Gly Arg Tyr Ile Thr
            100                 105                 110

Ala Glu Asp Val Gly Thr Thr Val Glu Asp Met Asp Ile Ile His Asp
        115                 120                 125

Glu Thr Asp Tyr Val Thr Gly Ile Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Ala Ala Phe Gly Thr Asp Ser Leu Glu Gly Lys Thr Ile
                165                 170                 175
```

```
Ala Val Gln Gly Val Gly Asn Val Ala Tyr Asn Leu Cys Arg His Leu
            180                 185                 190

His Glu Glu Gly Ala Asn Leu Ile Val Thr Asp Ile Asn Lys Gln Ser
        195                 200                 205

Val Gln Arg Ala Val Glu Asp Phe Gly Ala Arg Ala Val Asp Pro Asp
    210                 215                 220

Asp Ile Tyr Ser Gln Asp Cys Asp Ile Tyr Ala Pro Cys Ala Leu Gly
225                 230                 235                 240

Ala Thr Ile Asn Asp Asp Thr Ile Lys Gln Leu Lys Ala Lys Val Ile
                245                 250                 255

Ala Gly Ala Ala Asn Asn Gln Leu Lys Glu Thr Arg His Gly Asp Gln
            260                 265                 270

Ile His Glu Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Ala Glu
    290                 295                 300

Arg Ala Leu Lys Lys Val Glu Gly Ile Tyr Gly Asn Ile Glu Arg Val
305                 310                 315                 320

Leu Glu Ile Ser Gln Arg Asp Gly Ile Pro Ala Tyr Leu Ala Ala Asp
                325                 330                 335

Arg Leu Ala Glu Glu Arg Ile Glu Arg Met Arg Arg Ser Arg Ser Gln
            340                 345                 350

Phe Leu Gln Asn Gly His Ser Val Leu Ser Arg Arg
        355                 360


<210> SEQ ID NO 16
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Any amino acid except Leu

<400> SEQUENCE: 16

Met Glu Leu Phe Arg Tyr Met Glu Gln Tyr Asp Tyr Glu Gln Leu Val
1               5                   10                  15

Phe Cys Gln Asp Lys Gln Ser Gly Leu Lys Ala Ile Ile Ala Ile His
            20                  25                  30

Asp Thr Thr Leu Gly Pro Ala Xaa Gly Gly Thr Arg Met Trp Thr Tyr
        35                  40                  45

Glu Ser Glu Glu Ala Ala Ile Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Glu Met Phe
                85                  90                  95

Arg Ala Phe Gly Arg Tyr Ile Gln Gly Leu Asn Gly Arg Tyr Ile Thr
            100                 105                 110

Ala Glu Asp Val Gly Thr Thr Val Glu Asp Met Asp Ile Ile His Asp
        115                 120                 125

Glu Thr Asp Phe Val Thr Gly Ile Ser Pro Ala Phe Gly Ser Ser Gly
    130                 135                 140
```

Asn Pro Ser Pro Val Thr Ala Tyr Gly Val Tyr Lys Gly Met Lys Ala
145 150 155 160

Ala Ala Lys Ala Ala Phe Gly Thr Asp Ser Leu Glu Gly Lys Thr Val
165 170 175

Ala Val Gln Gly Val Gly Asn Val Ala Tyr Asn Leu Cys Arg His Leu
180 185 190

His Glu Glu Gly Ala Lys Leu Ile Val Thr Asp Ile Asn Lys Glu Ala
195 200 205

Val Glu Arg Ala Val Ala Glu Phe Gly Ala Arg Ala Val Asp Pro Asp
210 215 220

Asp Ile Tyr Ser Gln Glu Cys Asp Ile Tyr Ala Pro Cys Ala Leu Gly
225 230 235 240

Ala Thr Ile Asn Asp Asp Thr Ile Pro Gln Leu Lys Ala Lys Val Ile
245 250 255

Ala Gly Ala Ala Asn Asn Gln Leu Lys Glu Thr Arg His Gly Asp Gln
260 265 270

Ile His Asp Met Gly Ile Val Tyr Ala Pro Asp Tyr Val Ile Asn Ala
275 280 285

Gly Gly Val Ile Asn Val Ala Asp Glu Leu Tyr Gly Tyr Asn Ser Glu
290 295 300

Arg Ala Leu Lys Lys Val Glu Gly Ile Tyr Gly Asn Ile Glu Arg Val
305 310 315 320

Leu Glu Ile Ser Lys Arg Asp Arg Ile Pro Thr Tyr Leu Ala Ala Asp
325 330 335

Arg Leu Ala Glu Glu Arg Ile Glu Arg Met Arg Gln Ser Arg Ser Gln
340 345 350

Phe Leu Gln Asn Gly His His Ile Leu Ser Arg Arg
355 360

<210> SEQ ID NO 17
<211> LENGTH: 367
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (40)..(40)
<223> OTHER INFORMATION: Any amino acid except Leu

<400> SEQUENCE: 17

Met Glu Leu Phe Lys Tyr Met Glu Thr Tyr Asp Tyr Glu Gln Val Leu
1 5 10 15

Phe Cys Gln Asp Lys Glu Ser Gly Leu Lys Ala Ile Ile Ala Ile His
20 25 30

Asp Thr Thr Leu Gly Pro Ala Xaa Gly Gly Thr Arg Met Trp Met Tyr
35 40 45

Asn Ser Glu Glu Glu Ala Leu Glu Asp Ala Leu Arg Leu Ala Arg Gly
50 55 60

Met Thr Tyr Lys Asn Ala Ala Ala Gly Leu Asn Leu Gly Gly Gly Lys
65 70 75 80

Thr Val Ile Ile Gly Asp Pro Arg Lys Asp Lys Asn Glu Ala Met Phe
85 90 95

Arg Ala Phe Gly Arg Phe Ile Gln Gly Leu Asn Gly Arg Tyr Ile Thr
100 105 110

Ala Glu Asp Val Gly Thr Thr Val Ala Asp Met Asp Ile Ile Tyr Gln

```
        115                 120                 125

Glu Thr Asp Tyr Val Thr Gly Ile Ser Pro Glu Phe Gly Ser Ser Gly
    130                 135                 140

Asn Pro Ser Pro Ala Thr Ala Tyr Gly Val Tyr Arg Gly Met Lys Ala
145                 150                 155                 160

Ala Ala Lys Glu Ala Phe Gly Ser Asp Ser Leu Glu Gly Lys Val Val
                165                 170                 175

Ala Val Gln Gly Val Gly Asn Val Ala Tyr His Leu Cys Arg His Leu
            180                 185                 190

His Glu Glu Gly Ala Lys Leu Ile Val Thr Asp Ile Asn Lys Glu Val
        195                 200                 205

Val Ala Arg Ala Val Glu Glu Phe Gly Ala Lys Ala Val Asp Pro Asn
    210                 215                 220

Asp Ile Tyr Gly Val Glu Cys Asp Ile Phe Ala Pro Cys Ala Leu Gly
225                 230                 235                 240

Gly Ile Ile Asn Asp Gln Thr Ile Pro Gln Leu Lys Ala Lys Val Ile
                245                 250                 255

Ala Gly Ser Ala Asp Asn Gln Leu Lys Glu Pro Arg His Gly Asp Ile
            260                 265                 270

Ile His Glu Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Arg Glu
    290                 295                 300

Arg Ala Met Lys Lys Ile Glu Gln Ile Tyr Asp Asn Ile Glu Lys Val
305                 310                 315                 320

Phe Ala Ile Ala Lys Arg Asp Asn Ile Pro Thr Tyr Val Ala Ala Asp
                325                 330                 335

Arg Met Ala Glu Glu Arg Ile Glu Thr Met Arg Lys Ala Arg Ser Pro
            340                 345                 350

Phe Leu Gln Asn Gly His His Ile Leu Ser Arg Arg Arg Ala Arg
        355                 360                 365


<210> SEQ ID NO 18
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Any amino acid except Leu

<400> SEQUENCE: 18

Met Glu Ile Phe Lys Tyr Met Glu Lys Tyr Asp Tyr Glu Gln Leu Val
1               5                   10                  15

Phe Cys Gln Asp Glu Ala Ser Gly Leu Lys Ala Ile Ile Ala Ile His
            20                  25                  30

Asp Thr Thr Leu Gly Pro Ala Xaa Gly Gly Ala Arg Met Trp Thr Tyr
        35                  40                  45

Ala Thr Glu Glu Asn Ala Ile Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Phe Lys Asp Lys Asn Glu Glu Met Phe
                85                  90                  95
```

```
Arg Ala Leu Gly Arg Phe Ile Gln Gly Leu Asn Gly Arg Tyr Ile Thr
            100                 105                 110

Ala Glu Asp Val Gly Thr Thr Val Thr Asp Met Asp Leu Ile His Glu
        115                 120                 125

Glu Thr Asn Tyr Val Thr Gly Ile Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Glu Ala Phe Gly Thr Asp Met Leu Glu Gly Arg Thr Ile
                165                 170                 175

Ser Val Gln Gly Leu Gly Asn Val Ala Tyr Lys Leu Cys Glu Tyr Leu
            180                 185                 190

His Asn Glu Gly Ala Lys Leu Val Val Thr Asp Ile Asn Gln Ala Ala
        195                 200                 205

Ile Asp Arg Val Val Asn Asp Phe Gly Ala Thr Ala Val Ala Pro Asp
    210                 215                 220

Glu Ile Tyr Ser Gln Glu Val Asp Ile Phe Ser Pro Cys Ala Leu Gly
225                 230                 235                 240

Ala Ile Leu Asn Asp Glu Thr Ile Pro Gln Leu Lys Ala Lys Val Ile
                245                 250                 255

Ala Gly Ser Ala Asn Asn Gln Leu Gln Asp Ser Arg His Gly Asp Tyr
            260                 265                 270

Leu His Glu Leu Gly Ile Val Tyr Ala Pro Asp Tyr Val Ile Asn Ala
        275                 280                 285

Gly Gly Val Ile Asn Val Ala Asp Glu Leu Tyr Gly Tyr Asn Arg Glu
    290                 295                 300

Arg Ala Leu Lys Arg Val Asp Gly Ile Tyr Asp Ser Ile Glu Lys Ile
305                 310                 315                 320

Phe Glu Ile Ser Lys Arg Asp Ser Ile Pro Thr Tyr Val Ala Ala Asn
                325                 330                 335

Arg Leu Ala Glu Glu Arg Ile Ala Arg Val Ala Lys Ser Arg Ser Gln
            340                 345                 350

Phe Leu Lys Asn Glu Lys Asn Ile Leu Asn Gly Arg
        355                 360


<210> SEQ ID NO 19
<211> LENGTH: 3
<212> TYPE: PRT
<213> ORGANISM: Unknown
<220> FEATURE:
<223> OTHER INFORMATION: Description of Unknown: bacterial leucine
      dehydrogenase conserved region peptide

<400> SEQUENCE: 19

Asn Val Ala
1


<210> SEQ ID NO 20
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Thr Leu Glu Ile Phe Glu Tyr Leu Glu Lys Tyr Asp Tyr Glu Gln
1               5                   10                  15
```

-continued

```
Val Val Phe Cys Gln Asp Lys Glu Ser Gly Leu Lys Ala Ile Ile Ala
            20                  25                  30

Ile His Asp Thr Thr Leu Gly Pro Ala Ala Gly Gly Thr Arg Met Trp
        35                  40                  45

Thr Tyr Asp Ser Glu Glu Ala Ala Ile Glu Asp Ala Leu Arg Leu Ala
    50                  55                  60

Lys Gly Met Thr Tyr Lys Asn Ala Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160

Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
    210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
            260                 265                 270

Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
    290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335

Ala Asp Arg Leu Ala Glu Glu Arg Ile Ala Ser Leu Lys Asn Ser Arg
            340                 345                 350

Ser Thr Tyr Leu Arg Asn Gly His Asp Ile Ile Ser Arg Arg
        355                 360                 365
```